United States Patent
Samuelson et al.

(10) Patent No.: US 7,011,966 B2
(45) Date of Patent: Mar. 14, 2006

(54) **METHOD FOR CLONING AND EXPRESSION OF ACUI RESTRICTION ENDONUCLEASE AND ACUI METHYLASE IN *E. COLI***

(75) Inventors: James Samuelson, Danvers, MA (US); Shuang-yong Xu, Lexington, MA (US); Diana O'Loane, Beverly, MA (US)

(73) Assignee: New England Biolabs, Inc., Ipswich, MA (US)

(*) Notice: Subject to any disclaimer, the term of this patent is extended or adjusted under 35 U.S.C. 154(b) by 427 days.

(21) Appl. No.: 10/417,293

(22) Filed: Apr. 16, 2003

(65) Prior Publication Data

US 2004/0209257 A1 Oct. 21, 2004

(51) Int. Cl.
*C12N 9/22* (2006.01)
*C12N 15/55* (2006.01)

(52) U.S. Cl. .................. 435/199; 435/320.1; 435/252.3; 536/23.2

(58) Field of Classification Search ................ 435/199, 435/320.1, 252.3; 536/23.2
See application file for complete search history.

(56) References Cited

U.S. PATENT DOCUMENTS

| 5,200,333 A | 4/1993 | Wilson | 435/172.3 |
| 5,498,535 A | 3/1996 | Fomenkov et al. | 435/172.3 |

OTHER PUBLICATIONS

Roberts, et al. Nucleic Acids Res. 31:418–420 (2003).
Kosykh, et al., Mol. Gen. Genet. 178:717–719 (1980).
Mann, et al. Gene, 3:97–112 (1978).
Walder, et al., Proc. Nat. Acad. Sci. USA 78:1503–1507 (1981).
Bougueleret, et al., Nucl. Acids Res. 12:3659–3676 (1984).
Gingeras and Brooks, Proc. Natl. Acad. Sci. USA 80:402–406 (1983).
Theriault and roy, Gene 19:355–359 (1982).
Blumenthal, et al., J. Bacteriol. 164:501–509 (1985).
Wayne, et al. Gene 202:83–88 (1997).
Kiss, et al., Nucl. Acids Res. 13:6403–6421 (1985).
Szomolanyi, et al., Gene 10:219–225 (1980).
Janulaitis, et al., Gene 20:197–204 (1982).
Kiss and Baldauf, Gene 21:111–119 (1983).
Walder, et al., J. Biol. Chem. 258:1235–1241 (1983).
Fomenkov, et al., Nucl. Acids Res. 222:2399–2403 (1994).
Malone, et al., J. Mol. Biol. 253:618–632 (1995).
New England Biolabs Catalog 2002–2003, p. 252.
Kong, et al., Nucl. Acids Res. 28:3216–3223 (2000).
Janulaitis, et al., Nucl. Acids Res. 20:6043–6049 (1992).
Pingoud and Jeitsch, Nucl. Acids Res. 29:3705–3727 (2001).

*Primary Examiner*—Charles L. Patterson, Jr.
(74) *Attorney, Agent, or Firm*—Gregory D. Williams; Harriet M. Strimpel

(57) ABSTRACT

The present invention relates to recombinant DNA encoding the AcuI restriction endonuclease as well as AcuI methylase, and expression of AcuI restriction endonuclease and AcuI methylase in *E. coli* cells containing the recombinant DNA.

6 Claims, 8 Drawing Sheets

Figure 3

```
      ATGAAGCTCATTAAAGATGCATCTGCCGAAAAATTACGTGGCGGGTTTTATACACCTGAG
  1   ---------+---------+---------+---------+---------+---------+    60
      M  K  L  I  K  D  A  S  A  E  K  L  R  G  G  F  Y  T  P  E
      CCAATTGCTGCATTTATTCTAAAATGGGGAATAAATGGTAGTTCTGATTATGACATCTTA
 61   ---------+---------+---------+---------+---------+---------+   120
      P  I  A  A  F  I  L  K  W  G  I  N  G  S  S  D  Y  D  I  L
      GAACCAAGTTGTGGTGATGGTGTGTTTTAGAACAACTAAAGAAGAAAGATTTCTGTTTT
121   ---------+---------+---------+---------+---------+---------+   180
      E  P  S  C  G  D  G  V  F  L  E  Q  L  K  K  K  D  F  C  F
      CAATCTGTTACTGCTATCGAATTCGATACTATTGAAGCGAATAAAGCGAACCAAATTGAT
181   ---------+---------+---------+---------+---------+---------+   240
      Q  S  V  T  A  I  E  F  D  T  I  E  A  N  K  A  N  Q  I  D
      ATTGCTAATAAAAAGTAATCAATCAGGATTTTCATTTATATTGTAATACAACATCTCAA
241   ---------+---------+---------+---------+---------+---------+   300
      I  A  N  K  K  V  I  N  Q  D  F  H  L  Y  C  N  T  T  S  Q
      AAATTTGATCTTGTAGTCGGTAATCCTCCATATATTCGTTATCAATATTTTGATAAGAGT
301   ---------+---------+---------+---------+---------+---------+   360
      K  F  D  L  V  V  G  N  P  P  Y  I  R  Y  Q  Y  F  D  K  S
      CAACAGATTGAAGCAGATAAAATATTTAAAAAGGCTGGGTTAAAATATTCTAAATTAACA
361   ---------+---------+---------+---------+---------+---------+   420
      Q  Q  I  E  A  D  K  I  F  K  K  A  G  L  K  Y  S  K  L  T
      AATGCTTGGGTATCATTTATTGTTGGTTCTAGTTTATTGCTAAAAGAAAAAGGCAAAATA
421   ---------+---------+---------+---------+---------+---------+   480
      N  A  W  V  S  F  I  V  G  S  S  L  L  L  K  E  K  G  K  I
      GGTTTTGTTGTTCCAGCAGAATTGTTGCAAGTATCTTACGCTCAACAGCTCCGAGAATTT
481   ---------+---------+---------+---------+---------+---------+   540
      G  F  V  V  P  A  E  L  L  Q  V  S  Y  A  Q  Q  L  R  E  F
      TTGGCACATTTTTACAATAAAATTAATATTATTTCTTTTGAAAAATTAGTTTTTCCTGAT
541   ---------+---------+---------+---------+---------+---------+   600
      L  A  H  F  Y  N  K  I  N  I  I  S  F  E  K  L  V  F  P  D
      ATTCAGCAGGAAGTCGTACTACTATTGTGTGAAAAGAATAGTGATACTACCCATTTGATA
601   ---------+---------+---------+---------+---------+---------+   660
      I  Q  Q  E  V  V  L  L  L  C  E  K  N  S  D  T  T  H  L  I
      GAACATCTTGAATTAAAAGATGCCTCTGATCTTGAAAAACTGGATGTGAACCTTTTAAAG
661   ---------+---------+---------+---------+---------+---------+   720
      E  H  L  E  L  K  D  A  S  D  L  E  K  L  D  V  N  L  L  K
      AGTCCTCGTAAACAGATTGATTTCAAATCTAATAAATGGACTTATTATTTCTTAGAGCAA
721   ---------+---------+---------+---------+---------+---------+   780
      S  P  R  K  Q  I  D  F  K  S  N  K  W  T  Y  Y  F  L  E  Q
      GAAGAGATTGATTTCTTGAAAATATTGCTGAAAGAAAAATATTCCAATATTAGGTGAT
781   ---------+---------+---------+---------+---------+---------+   840
      E  E  I  D  F  L  E  N  I  A  E  R  K  N  I  P  I  L  G  D
      TTTGCAGATGTAGAAGTAGGAATTACTACAGGAGCAAATAGCTATTTTACTGTGCCTATT
841   ---------+---------+---------+---------+---------+---------+   900
      F  A  D  V  E  V  G  I  T  T  G  A  N  S  Y  F  T  V  P  I
      TCAACTGTAAAAGAATTTAATCTTGAACAATTTGCTAAGCCTATGGTTGGTCGTAGTGTA
901   ---------+---------+---------+---------+---------+---------+   960
      S  T  V  K  E  F  N  L  E  Q  F  A  K  P  M  V  G  R  S  V
      CAAGTGAACAGTATCACGTTTACTGAGAGTGACTGGTTACAGAACTTACAAATGGAAGCA
961   ---------+---------+---------+---------+---------+---------+  1020
      Q  V  N  S  I  T  F  T  E  S  D  W  L  Q  N  L  Q  M  E  A
      AAAGCAAATTTATTGGTTTTCCCAAATCGTAATCAAATTTCTAATCATAGTGGTGCGAAT
1021  ---------+---------+---------+---------+---------+---------+  1080
      K  A  N  L  L  V  F  P  N  R  N  Q  I  S  N  H  S  G  A  N
      AAATATATTGAATATGGTGAAGAACTGGGAGTTAACAAGGGATATAAGACACGTATTCGT
1081  ---------+---------+---------+---------+---------+---------+  1140
      K  Y  I  E  Y  G  E  E  L  G  V  N  K  G  Y  K  T  R  I  R
      GATGACTGGTTTGTTATTCCATCTATTAAGTTGTCAGACGCTTTGTTTATTCGTAGAAAT
1141  ---------+---------+---------+---------+---------+---------+  1200
      D  D  W  F  V  I  P  S  I  K  L  S  D  A  L  F  I  R  R  N
      AACCTGTTCCCACGACTTATTTTGAATGAAGCCCAAGCATATACAACAGATACGATGCAT
1201  ---------+---------+---------+---------+---------+---------+  1260
      N  L  F  P  R  L  I  L  N  E  A  Q  A  Y  T  T  D  T  M  H
      CGAGTTTTTATTAAACAGGAAACTAATAAGCAGGCTTTTATTGCTAGCTTTTATAATTCT
1261  ---------+---------+---------+---------+---------+---------+  1320
      R  V  F  I  K  Q  E  T  N  K  Q  A  F  I  A  S  F  Y  N  S
```

Figure 3 - continued

```
      TTATCTTTAGCCTTTTCTGAGATTGTTGGTCGTAGCTATGGTGGTGGTGTCTTGGAATTA
1321  ------------+---------+---------+---------+---------+---------+  1380
      L  S  L  A  F  S  E  I  V  G  R  S  Y  G  G  G  V  L  E  L
      ATGCCGAGTGAAGCAGCAAGAATTTTACTACCTTATCAAGTTGATAATGATAAGTTCTTG
1381  ------------+---------+---------+---------+---------+---------+  1440
      M  P  S  E  A  A  R  I  L  L  P  Y  Q  V  D  N  D  K  L  L
      GATCAGATTGATAAATTAATGCGTGAAAAAAGAAGTATTGATGATATCTTACATATTTCT
1441  ------------+---------+---------+---------+---------+---------+  1500
      D  Q  I  D  K  L  M  R  E  K  R  S  I  D  D  I  L  H  I  S
      AATGATATTATTCTTCGACAAGCATATGGTTTTTCAAAAAAAGAAATTGAACTTGCAGAT
1501  ------------+---------+---------+---------+---------+---------+  1560
      N  D  I  I  L  R  Q  A  Y  G  F  S  K  K  E  I  E  L  A  D
      CGAATTTGGAAGAAATTATCTGCAAGGAGATTGAATAGGGGGAAATAA
1561  ------------+---------+---------+---------+--------  1608
      R  I  W  K  K  L  S  A  R  R  L  N  R  G  K  *
```

Figure 4

```
     GTGGTTCATGATCATAAGCTTGAATTAGCCAAACTTATTCGCAACTATGAGACGAATAGA
  1  ------------------------------------------------------------   60
     V  V  H  D  H  K  L  E  L  A  K  L  I  R  N  Y  E  T  N  R
     AAAGAATGTCTAAATTCTAGATATAATGAAACACTTTTACGAAGTGATTATCTTGATCCA
 61  ------------------------------------------------------------  120
     K  E  C  L  N  S  R  Y  N  E  T  L  L  R  S  D  Y  L  D  P
     TTTTTTGAACTTCTTGGCTGGGATATTAAAAATAAAGCTGGAAAACCGACTAATGAAAGA
121  ------------------------------------------------------------  180
     F  F  E  L  L  G  W  D  I  K  N  K  A  G  K  P  T  N  E  R
     GAGGTTGTCTTGGAACAGGCACTTAAAGCAAGTGCATCTGAACATTCTAAAAAACCAGAT
181  ------------------------------------------------------------  240
     E  V  V  L  E  E  A  L  K  A  S  A  S  E  H  S  K  K  P  D
     TATACATTCAGACTTTTTTCTGAAAGAAAGTTTTTCTTGGAAGCTAAAAAACCATCAGTT
241  ------------------------------------------------------------  300
     Y  T  F  R  L  F  S  E  R  K  F  F  L  E  A  K  K  P  S  V
     CATATTGAATCGGATAATGAAACTGCTAAACAAGTGCGAAGATATGGCTTTACCGCCAAA
301  ------------------------------------------------------------  360
     H  I  E  S  D  N  E  T  A  K  Q  V  R  R  Y  G  F  T  A  K
     CTAAAAATTTCAGTTTTATCAAATTTTGAATATTTAGTTATTTATGATACCTCTGTAAAG
361  ------------------------------------------------------------  420
     L  K  I  S  V  L  S  N  F  E  Y  L  V  I  Y  D  T  S  V  K
     GTTGATGGTGATGATACCTTTAATAAGGCACGTATAAAAAAATACCATTACACAGAGTAT
421  ------------------------------------------------------------  480
     V  D  G  D  D  T  F  N  K  A  R  I  K  K  Y  H  Y  T  E  Y
     GAAACTCACTTTGATGAAATTTGTGACTTATTAGGAAGAGAGTCCGTTTACTCTGGGAAT
481  ------------------------------------------------------------  540
     E  T  H  F  D  E  I  C  D  L  L  G  R  E  S  V  Y  S  G  N
     TTTGATAAAGAATGGTTGAGTATCGAAAATAAAATTAATCACTTTTCTGTAGATACCTTA
541  ------------------------------------------------------------  600
     F  D  K  E  W  L  S  I  E  N  K  I  N  H  F  S  V  D  T  L
     TTTTTAAAACAGATTAATACATGGCGTCTATTGCTTGGTGAAGAAATCTATAAGTATCAA
601  ------------------------------------------------------------  660
     F  L  K  Q  I  N  T  W  R  L  L  L  G  E  E  I  Y  K  Y  Q
     CCTACGATACAAGAGAATGAGCTTAATGACATTGTACAGAGCTATCTGAATAGAATTATT
661  ------------------------------------------------------------  720
     P  T  I  Q  E  N  E  L  N  D  I  V  Q  S  Y  L  N  R  I  I
     TTTTTGAGAGTCTGTGAAGATAGAAATTTAGAGACTTATCAGACATTACTGAATTTTGCT
721  ------------------------------------------------------------  780
     F  L  R  V  C  E  D  R  N  L  E  T  Y  Q  T  L  L  N  F  A
     TCAAGTAATGATTTCTCCGCTCTTATTGATAAGTTTAAGCAGGCAGATCGTTGCTATAAT
781  ------------------------------------------------------------  840
     S  S  N  D  F  S  A  L  I  D  K  F  K  Q  A  D  R  C  Y  N
     TCAGGCCTATTTGATCAATTGCTTACAGAGCAAATTATTGAGGATATTAGTTCTGTATTT
841  ------------------------------------------------------------  900
     S  G  L  F  D  Q  L  L  T  E  Q  I  I  E  D  I  S  S  V  F
     TGGGTAATCATTAAGCAATTATATTATCCAGAAAGTCCTTATTCATTTAGTGTGTTCTCT
901  ------------------------------------------------------------  960
     W  V  I  I  K  Q  L  Y  Y  P  E  S  P  Y  S  F  S  V  F  S
     TCGGATATTTTAGGTAATATTTACGAAATATTTTTATCTGAGAAATTAGTAATTAATCAA
961  ------------------------------------------------------------ 1020
     S  D  I  L  G  N  I  Y  E  I  F  L  S  E  K  L  V  I  N  Q
     AGCAGAGTTGAGTTAGTCAAGAAACCAGAGAATTTAGATAGAGACATTGTCACAACACCA
1021 ------------------------------------------------------------ 1080
     S  R  V  E  L  V  K  K  P  E  N  L  D  R  D  I  V  T  T  P
     ACCTTTATTATTAATGACATCTTGAGAAATACGGTTCTACCGAAGTGCTATGGAAAAACA
1081 ------------------------------------------------------------ 1140
     T  F  I  I  N  D  I  L  R  N  T  V  L  P  K  C  Y  G  K  T
     GATATAGAAATTCTACAGCTAAAATTTGCTGATATTGCTTGTGGTTCGGGAGCATTTTTA
1141 ------------------------------------------------------------ 1200
     D  I  E  I  L  Q  L  K  F  A  D  I  A  C  G  S  G  A  F  L
     CTGGAGTTGTTCCAATTACTTAATGATACTCTAGTTGACTATTATTTAAGTAGTGATACT
1201 ------------------------------------------------------------ 1260
     L  E  L  F  Q  L  L  N  D  T  L  V  D  Y  Y  L  S  S  D  T
     TCTCAATTAATTCCAACAGGTATCGGTACTTATAAGCTGTCTTATGAAATCAAGAGAAAG
1261 ------------------------------------------------------------ 1320
     S  Q  L  I  P  T  G  I  G  T  Y  K  L  S  Y  E  I  K  R  K
```

Figure 4 - continued

```
      GTTCTATTAAGTTGTATTTTTGGCATAGATAAGGACTTAAATGCTGTAGAGGCTGCAAAG
1321  ---------+---------+---------+---------+---------+---------+  1380
      V  L  L  S  C  I  F  G  I  D  K  D  L  N  A  V  E  A  A  K
      TTCGGATTGTTGCTAAAATTATTAGAGGGTGAAGACGTACAATCTATAGCTAATATTAGA
1381  ---------+---------+---------+---------+---------+---------+  1440
      F  G  L  L  L  K  L  L  E  G  E  D  V  Q  S  I  A  N  I  R
      CCAGTTCTCCCAGATTTATTAGATAACATACTTTTTGGTAACAGTTTATTAGAACCAGAA
1441  ---------+---------+---------+---------+---------+---------+  1500
      P  V  L  P  D  L  L  D  N  I  L  F  G  N  S  L  L  E  P  E
      AAAGTCGAGCTTGATCATCAGGTAGAAGTAAATCCGTTAGATTTTTCTGATTTAAAGTTT
1501  ---------+---------+---------+---------+---------+---------+  1560
      K  V  E  L  D  H  Q  V  E  V  N  P  L  D  F  S  D  L  K  F
      GATGTAATTGTTGGCAACCCTCCATATATGAAATCAGAGGATATGAAGAATATTACTCCT
1561  ---------+---------+---------+---------+---------+---------+  1620
      D  V  I  V  G  N  P  P  Y  M  K  S  E  D  M  K  N  I  T  P
      TTGGAGTTACCTTTATATAAGAAAAACTATGTTTCTGCTTATAAGCAATTTGATAAATAT
1621  ---------+---------+---------+---------+---------+---------+  1680
      L  E  L  P  L  Y  K  K  N  Y  V  S  A  Y  K  Q  F  D  K  Y
      TTCTTGTTCTTAGAGCGGGGTTTAGCTCTATTAAAAGAAGAGGGAATACTTGGATATATT
1681  ---------+---------+---------+---------+---------+---------+  1740
      F  L  F  L  E  R  G  L  A  L  L  K  E  E  G  I  L  G  Y  I
      GTTCCAAGTAAATTTACTAAAGTGGGTGCAGGGAAAAAGTTACGGGAATTACTAACAGAT
1741  ---------+---------+---------+---------+---------+---------+  1800
      V  P  S  K  F  T  K  V  G  A  G  K  K  L  R  E  L  L  T  D
      AAGGGTTATCTTGACTCTATTGTTTCTTTTGGTGCTAATCAAATATTTCAGGATAAAACA
1801  ---------+---------+---------+---------+---------+---------+  1860
      K  G  Y  L  D  S  I  V  S  F  G  A  N  Q  I  F  Q  D  K  T
      ACTTATACTTGTTTACTTATTTTAAGAAAAACTCCTCATACTGATTTTAAATATGCAGAG
1861  ---------+---------+---------+---------+---------+---------+  1920
      T  Y  T  C  L  L  I  L  R  K  T  P  H  T  D  F  K  Y  A  E
      GTTCGTAATTTAATTGACTGGAAAGTGCGTAAAGCTGATGCTATGGAATTTTCCTCTCAA
1921  ---------+---------+---------+---------+---------+---------+  1980
      V  R  N  L  I  D  W  K  V  R  K  A  D  A  M  E  F  S  S  Q
      CAACTGAGTACATTGCAAAGTGATGCGTGGATTTTAATTCCATCTGAATTAATCTCAGTT
1981  ---------+---------+---------+---------+---------+---------+  2040
      Q  L  S  T  L  Q  S  D  A  W  I  L  I  P  S  E  L  I  S  V
      TATCATCAGATATTAGCACAAAGCCAAAAGCTAGAGGATATTGTCGGTATTGATAATATA
2041  ---------+---------+---------+---------+---------+---------+  2100
      Y  H  Q  I  L  A  Q  S  Q  K  L  E  D  I  V  G  I  D  N  I
      TTTAATGGGATTCAAACCAGTGCTAATGATGTCTATATTTTTGTGCCAACTCATGAGGAT
2101  ---------+---------+---------+---------+---------+---------+  2160
      F  N  G  I  Q  T  S  A  N  D  V  Y  I  F  V  P  T  H  E  D
      ACTGAAAACTATTATTTTATAAAGAAAGGACAAGAGTACAAAATTGAAAGGAAATTACG
2161  ---------+---------+---------+---------+---------+---------+  2220
      T  E  N  Y  Y  F  I  K  K  G  Q  E  Y  K  I  E  K  E  I  T
      AAGCCTTATTTTAAAACAACGAGTGGTGAGGATAACTTATATACTTACCGTACTTTCAAG
2221  ---------+---------+---------+---------+---------+---------+  2280
      K  P  Y  F  K  T  T  S  G  E  D  N  L  Y  T  Y  R  T  F  K
      CCTAATGCTCGAGTCATTTATCCGTATACTCAAACTGAGAGTAGTGTAGAACTAATTCCT
2281  ---------+---------+---------+---------+---------+---------+  2340
      P  N  A  R  V  I  Y  P  Y  T  Q  T  E  S  S  V  E  L  I  P
      TTAGATGAAATACGAGAAATTTTTCCTTTAGCATACAAATATTTAATGTCGCTTAAGTTC
2341  ---------+---------+---------+---------+---------+---------+  2400
      L  D  E  I  R  E  I  F  P  L  A  Y  K  Y  L  M  S  L  K  F
      GTTTTAAGTAGCCCCAAACGAGATATAAAACCTAGACCTAAAACAACAAATGAATGGCAT
2401  ---------+---------+---------+---------+---------+---------+  2460
      V  L  S  S  P  K  R  D  I  K  P  R  P  K  T  T  N  E  W  H
      AGGTATGGACGGCATCAAAGTCTAGATAATTGTGGCTTGAGTCAGAAAATTATTGTAGGT
2461  ---------+---------+---------+---------+---------+---------+  2520
      R  Y  G  R  H  Q  S  L  D  N  C  G  L  S  Q  K  I  I  V  G
      GTGCTTTCAGTTGGTGATAAGTACGCTATAGATACTTATGGAACGTTGATTTCATCAGGC
2521  ---------+---------+---------+---------+---------+---------+  2580
      V  L  S  V  G  D  K  Y  A  I  D  T  Y  G  T  L  I  S  S  G
      GGTACGGCTGGATACTGTGTGGTTGCTCTTCCAGATGATTGTAAATATTCAATTTATTAT
2581  ---------+---------+---------+---------+---------+---------+  2640
      G  T  A  G  Y  C  V  V  A  L  P  D  D  C  K  Y  S  I  Y  Y
```

Figure 4 - continued

```
        TTACAGGCAATTTTAAACTCAAAATATTTAGAGTGGTTTAGTGCCTTACATGGAGAAGTT
2641    ---------+---------+---------+---------+---------+---------+    2700
        L  Q  A  I  L  N  S  K  Y  L  E  W  F  S  A  L  H  G  E  V

TTCCGAGGTGGTTATATTGCTAGGGGAACTAAGGTGCTTAAGAACTTGCCTATTAGGAAA
2701    ---------+---------+---------+---------+---------+---------+    2760
        F  R  G  G  Y  I  A  R  G  T  K  V  L  K  N  L  P  I  R  K

ATTGATTTTGATAATCTTGAAGAAGCAAATCTACATGATCTAATTGCGACCAAGCAAAAA
2761    ---------+---------+---------+---------+---------+---------+    2820
        I  D  F  D  N  L  E  E  A  N  L  H  D  L  I  A  T  K  Q  K

GAGCTTATAGAGATTTATGACAAAATAGATGTTAATGTAAATAATAAAAGAGTTCTGACC
2821    ---------+---------+---------+---------+---------+---------+    2880
        E  L  I  E  I  Y  D  K  I  D  V  N  V  N  N  K  R  V  L  T

CCATTGCAACGTATGTTTAAACGAGAGAAAGAGGTTTTAGACCAATTGTTGAGTCGACTG
2881    ---------+---------+---------+---------+---------+---------+    2940
        P  L  Q  R  M  F  K  R  E  K  E  V  L  D  Q  L  L  S  R  L

TATAACTTAGGTGTAGATGATTCCTTGATCCCTTATATTAAGGATTTGTATGAAGCTCAT
2941    ---------+---------+---------+---------+---------+---------+    3000
        Y  N  L  G  V  D  D  S  L  I  P  Y  I  K  D  L  Y  E  A  H

TAA
3001    ---    3003
```

US 7,011,966 B2

METHOD FOR CLONING AND EXPRESSION OF ACUI RESTRICTION ENDONUCLEASE AND ACUI METHYLASE IN E. COLI

BACKGROUND OF THE INVENTION

The present invention relates to recombinant DNA that encodes the AcuI restriction endonuclease (AcuI endonuclease or AcuIR) as well as the AcuI methyltransferase (AcuI methylase or M.AcuI), and expression of AcuI endonuclease and methylase in E. coli cells containing the recombinant DNA. AcuI is an isoschizomer of Eco57I (MBI Fermentas (Vilnius, Lithuania) product #ER0341).

Type II restriction endonucleases are a class of enzymes that occur naturally in bacteria and in some viruses. When they are purified away from other bacterial/viral proteins, restriction endonucleases can be used in the laboratory to cleave DNA molecules into small fragments for molecular cloning and gene characterization.

Restriction endonucleases recognize and bind to particular sequences of nucleotides (the 'recognition sequence') along DNA molecules. Once bound, they cleave the molecule within (e.g. BamHI), to one side of (e.g. SapI), or to both sides (e.g. TspRI) of the recognition sequence. Different restriction endonucleases have affinity for different recognition sequences. At least two hundred and forty restriction endonucleases with unique specificities have been identified among the many hundreds of bacterial species that have been examined to date (Roberts et al., *Nucl. Acids Res.* 31:418–420 (2002)).

Restriction endonucleases typically are named according to the bacteria from which they are discovered. Thus, the species *Deinococcus radiophilus* for example, produces three different restriction endonucleases, named DraI, DraII and DraIII. These enzymes recognize and cleave the sequences 5'TTT/AAA3', 5'RG/GNCCY3' and 5'CACNNN/GTG3' respectively. *Escherichia coli* RY13, on the other hand, produces only one enzyme, EcoRI, which recognizes the sequence 5'G/AATTC3'.

A second component of bacterial/viral restriction-modification (R-M) systems is the methylase. These enzymes co-exist with restriction endonucleases and they provide the means by which bacteria are able to protect their own DNA and distinguish it from foreign DNA. Modification methylases recognize and bind to the same recognition sequence as the corresponding restriction endonuclease, but instead of cleaving the DNA, they chemically modify one particular nucleotide within the sequence by the addition of a methyl group to produce C5 methyl cytosine, N4 methyl cytosine, or N6 methyl adenine. Following methylation, the recognition sequence is no longer cleaved by the cognate restriction endonuclease. The DNA of a bacterial cell is always fully modified by the activity of its modification methylase. It is therefore completely insensitive to the presence of the endogenous restriction endonuclease. Only unmodified, and therefore identifiable foreign DNA, is susceptible to restriction endonuclease recognition and cleavage. During and after DNA replication, usually hemi-methylated DNA (DNA methylated on one strand) is also resistant to the cognate restriction endonuclease.

With the advancement of recombinant DNA technology, it is now possible to clone genes and overproduce the enzymes in large quantities. The key to isolating clones of restriction endonuclease genes is to develop an efficient method to identify such clones within genomic DNA libraries, (i.e. populations of clones derived by 'shotgun' procedures) when they occur at frequencies as low as $10^{-3}$ to $10^{-4}$. Preferably, the method should be selective, such that the unwanted clones with non-methylase inserts are destroyed while the desirable rare clones survive.

A large number of type II restriction-modification systems have been cloned. The first cloning method used bacteriophage infection as a means of identifying or selecting restriction endonuclease clones (EcoRII: Kosykh et al., *Mol. Gen. Genet.* 178:717–719, (1980); HhaII: Mann et al., *Gene* 3:97–112, (1978); PstI: Walder et al., *Proc. Nat. Acad. Sci.* 78:1503–1507, (1981)). Since the expression of restriction-modification systems in bacteria enables them to resist infection by bacteriophages, cells that carry cloned restriction-modification genes can, in principle, be selectively isolated as survivors from genomic DNA libraries that have been exposed to phage. However, this method has been found to have only a limited success rate. Specifically, it has been found that cloned restriction-modification genes do not always confer sufficient phage resistance to achieve selective survival.

Another cloning approach involves transferring systems initially characterized as plasmid-borne into *E. coli* cloning vectors (EcoRV: Bougueleret et al., *Nucl. Acids. Res.* 12:3659–3676 (1984); PaeR7: Gingeras and Brooks, *Proc. Natl. Acad. Sci. USA* 80:402–406 (1983); Theriault and Roy, *Gene* 19:355–359 (1982); PvuII: Blumenthal et al., *J. Bacteriol.* 164:501–509 (1985); Tsp45I: Wayne et al. *Gene* 202:83–88 (1997)).

A third approach is to select for active expression of methylase genes (methylase selection) (U.S. Pat. No. 5,200,333 and BsuRI: Kiss et al., *Nucl. Acids. Res.* 13:6403–6421 (1985)). Since restriction-modification genes are often closely linked together, both genes can often be cloned simultaneously. This selection does not always yield a complete restriction system however, but instead yields only the methylase gene (BspRI: Szomolanyi et al., *Gene* 10:219–225 (1980); BcnI: Janulaitis et al., *Gene* 20:197–204 (1982); BsuRI: Kiss and Baldauf, *Gene* 21:111–119 (1983); and PstI: Walder et al., *J. Biol. Chem.* 258:1235–1241 (1983)).

A more recent method, the "endo-blue method", has been described for direct cloning of thermostable restriction endonuclease genes into *E. coli* based on an indicator strain of *E. coli* containing the dinD::lacZ fusion (U.S. Pat. No. 5,498,535; Fomenkov et al., *Nucl. Acids Res.* 22:2399–2403 (1994)). This method utilizes the *E. coli* SOS response signal following DNA damage caused by restriction endonucleases or non-specific nucleases. A number of thermostable nuclease genes (TaqI, Tth111I, BsoBI, Tf nuclease) have been cloned by this method (U.S. Pat. No. 5,498,535). The disadvantage of this method is that some positive blue clones containing a restriction endonuclease gene are difficult to culture due to the lack of the cognate methylase gene.

There are three major groups of DNA methyltransferases based on the position and the base that is modified (C5-cytosine methylases, N4-cytosine methylases, and N6-adenine methylases). N4-cytosine and N6-adenine methylases are amino-methyltransferases (Malone et al. *J. Mol. Biol.* 253:618–632 (1995)). When a restriction site on DNA is modified (methylated) by the methylase, it is resistant to digestion by the cognate restriction endonuclease. Sometimes methylation by a non-cognate methylase can also confer DNA sites resistant to restriction digestion. For example, Dcm methylase modification of 5' CCWGG 3' (W=A or T) can also make the DNA resistant to PspGI restriction digestion. Another example is that CpG methylase can modify the CG dinucleotide of the NotI site (5' GCGGCCGC 3') and make it refractory to NotI digestion (New England Biolabs' (Beverly, Mass.) catalog, 2002–03, page 252). Therefore methylases can be used as a tool to modify certain DNA sequences and make them uncleavable by restriction enzymes.

Type II methylase genes have been found in many sequenced bacterial genomes (GenBank, http://www.ncbi.nlm.nih.gov; and Rebase®, http://rebase.neb.com/rebase). Direct cloning and over-expression of ORFs adjacent to methylase genes yielded restriction enzymes with novel specificities (Kong et al. Nucl. Acids Res. 28:3216–3223 (2000)). Thus microbial genome mining emerged as a new way of screening/cloning new type II restriction enzymes and methylases and their isoschizomers.

Because purified restriction endonucleases and modification methylases are useful tools for creating recombinant DNA molecules in the laboratory, there is a strong commercial interest to obtain bacterial strains through recombinant DNA techniques that produce large quantities of restriction enzymes and methylases. Such over-expression strains should also simplify the task of enzyme purification.

AcuI recognizes the double-stranded DNA sequence 5'CTGAAG3' (or 5'CTTCAG3' bottom strand) and cleaves 16/14 bases downstream of its recognition sequence to generate a 2-base 3' cohesive end. AcuI is classified as a type IIs restriction enzyme since it cleaves DNA downstream from its recognition site. In addition, AcuI was expected to be a type IIG enzyme as it is an isoschizomer of Eco57I, the first such restriction enzyme to be identified (Janulaitis et al. Nucl. Acids. Res. 20:6043–6049 (1992)). Type IIG restriction endonucleases are distinguished by the fact that they possess both restriction and modification activity in one polypeptide chain (Pingoud and Jeltsch, Nucl. Acids Res. 29:3705–3727 (2001)). Therefore, when such an enzyme is employed in vitro to digest DNA, two competing activities are at work. If the modification (methylation) activity is significant, some of the substrate recognition sites may become modified before the endonuclease function is complete. This outcome is clearly apparent when using Eco57I to cleave lambda DNA, for example. (see FIG. 1). In contrast, when native purified AcuI is used to cleave the same substrate, complete digestion is observed. Therefore, an attempt was made to clone the AcuI restriction-modification system into E. coli in order to over-express and purify commercial quantities of the AcuI restriction endonuclease.

SUMMARY OF THE INVENTION

The present invention relates to a method for cloning the AcuI restriction endonuclease and AcuI methylase genes into E. Coli by methylase selection and inverse PCR amplification of the DNA adjacent to the AcuI methylase gene. AcuI endonuclease is native to the bacterium *Acinetobacter calcoaceticua* SRW4 (New England Biolabs strain #3307). Genomic DNA was isolated from this strain and several genomic DNA libraries were prepared. After digesting the libraries with native AcuI, the putative AcuI methylase gene was selected. The putative gene displayed high sequence similarity to the amino-methyltransferase family and notably to the eco57IM gene.

Assuming that the AcuI R-M gene organization would be similar to that of Eco57I, inverse PCR was performed to locate the AcuI endonuclease gene downstream from the methylase gene. A BLAST search of the downstream region revealed that the downstream DNA was homologous to the *Acinetobacter* ADP1 mismatch repair gene mutS. Therefore, inverse PCR efforts were redirected to the region upstream of the putative acuIM gene. After walking 3.0 kb upstream, the acuIRM gene was identified. Herein, acuIRM refers to the gene encoding the AcuI endonuclease-methylase fusion protein. Two rounds of inverse PCR were necessary to completely identify the acuIRM gene as the open reading frame is 3003 bp, which encodes a protein of 1000 amino acids with a calculated molecular weight of 115,826 daltons. As well, the acuIM open reading frame is relatively large at 1608 bp, encoding a protein of 535 amino acids with a calculated molecular weight of 61,458 daltons.

Construction of an AcuI overexpression strain proved to be very difficult due to the large size of the AcuI endonuclease gene and gene product. First of all, PCR amplification of a 3.0 kb gene is subject to the limitations of polymerase fidelity and processivity. After initially failing to isolate an active clone, KOD HiFi polymerase (Novagen (Madison, Wis.)) was employed to increase the probability of cloning a wild-type acuIRM gene. Secondly, over-expression of such a large polypeptide is limited in prokaryotic hosts such as *E. coli*. Furthermore, type IIG restriction enzymes possess relatively low specific activity so detection of an active enzyme within a cellular extract may be a limiting factor in the isolation of a recombinant clone. AcuI over-expression was attempted from a total of three vectors. Finally, a wild-type recombinant AcuI clone was isolated using pET28a as the expression vector and ER2744 as the T7 expression host. In order to premodify host ER2744, a 2.8 kb SalI fragment from an original methylase clone (ANS6) was subcloned into pACYC184 to create pACYC184-AcuIM clone #9. Therefore, the final over-expression strain was ER2744 [pET28a-AcuIRM, pACYC184-AcuIM]. This strain (NEB#1513) produces 17,400 units per gram of wet cells.

BRIEF DESCRIPTION OF THE DRAWINGS

FIG. 4 AcuI endonuclease gene sequence (SEQ ID NO:3) (acuIRM, 3003 bp) and the encoded amino acid sequence (SEQ ID NO:4).

DETAILED DESCRIPTION OF THE INVENTION

Figure 1:
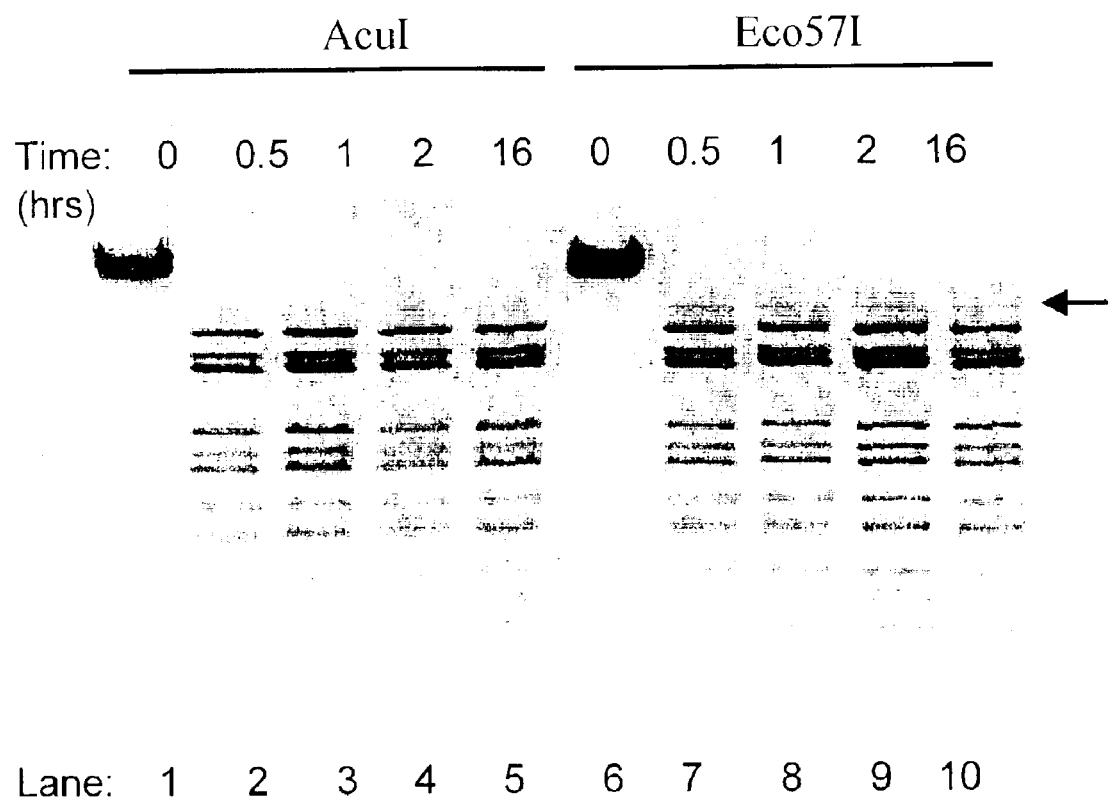
FIG. 1 Digestion properties of native AcuI as compared to recombinant Eco57I (Fermentas (Vilnius, Lithuania) product #ER0341). Five units of each enzyme were used to digest 1 μg of lambda DNA for 0.5, 1, 2 or 16 hours at 37° C. in the presence of 0.08 mM S-adenosylmethionine. An arrow indicates the incomplete digestion product remaining after incubation with Eco57I.

The method described herein by which the AcuI methylase and the AcuI endonuclease genes are preferably cloned and expressed in *E. coli* employs the following steps:

1. Preparation of Genomic DNA and Construction of Plasmid Libraries to Select a Functional AcuI Methylase Gene The first step in creating the recombinant AcuI R-M system in *E. coli* was to isolate a functional methylase gene in order to pre-protect the host genomic DNA against expression of the AcuI endonuclease gene. Vector pRRS (Skoglund et al. Gene 88: 1–5 (1990)) was linearized with either BamHI, EcoRI or SphI followed by CIP treatment. AcuI genomic DNA was purified from *Acinetobacter calcoaceticua* SRW4 (New England Biolabs strain #3307) by the standard procedure. AcuI genomic DNA (9 µg per reaction) was completely digested with BamHI, EcoRI or SphI or partially digested with ApoI, Sau3AI or NlaIII. The partial digests were optimized to yield DNA fragments in the 2–10 kb range. After gel purification of the six fragment types, each lot was ligated into vector pRRS. The BamHI and Sau3AI fragments were ligated into BamHI cut pRRS. The EcoRI and ApoI fragments were ligated into EcoRI cut pRRS. And the SphI and NlaIII fragments were ligated into SphI cut pRRS. The six ligation reactions were incubated overnight and then each was transformed into ER2502 by electroporation. Each transformation yielded >20,000 colonies. The colonies from the partial libraries were combined into one 500 mL culture and the colonies from the complete libraries were combined into a second 500 mL culture. After overnight incubation, plasmid DNA was prepared from each by the Qiagen (Studio City, Calif.) Maxiprep procedure. Fifty micrograms of each library (partial versus complete) were digested overnight with native AcuI. A sample of each digest was then analyzed by agarose gel electrophoresis and two shortcomings were revealed. First, the overnight digest was incomplete (due to excessive DNA) so this critical "challenge" step was unsuccessful. But most importantly, the partial AcuI digest revealed that a majority of the library DNA clones did not contain genomic DNA inserts. This outcome was most likely due to inadequate CIP treatment of vector PRRS. Therefore, new vector was prepared but pUC19 was substituted in place of pRRS. Vector pUC19 possesses two AcuI (Eco57I) sites, a necessary feature for the methylation selection procedure. Ten micrograms of pUC19 were digested with BamHI, EcoRI or SphI for 2 hrs at 37° C. Next, 5 units of CIP were added to each reaction for 30 min at 37° C. followed by heat-inactivation for 30 min at 65° C. Finally, the pUC19 vector DNA was purified by a Qiagen (Studio City, Calif.) miniprep spin column. The three vectors types were ligated with the six genomic DNA types as described above to create three partial and three complete AcuI genomic DNA libraries. The pUC19 ligations each yielded >30,000 colonies after transformation into ER2502 by electroporation (except the BamHI ligation yielded only 18,000 colonies). An aliquot of each ligation was separately transformed into ER2683 to conduct blue/white screening to assess the number of insert-containing clones. The percentage of inserts in each library varied from 50–87% (except the BamHI assessment found only 1 of 13 white colonies). Therefore, the BamHI library was excluded. The "complete" library was then created by inoculating approximately 10,000 colonies of each of the EcoRI and SphI libraries into 500 mL LB plus Amp, growing for 3 hours and isolating plasmid DNA by the Qiagen (Studio City, Calif.) Maxiprep procedure. The "partial" library was created in the same manner by pooling approximately 10,000 ApoI colonies, 10,000 NlaIII colonies and 20,000 Sau3AI colonies.

Each library (5 µg) was challenged with 20 units of native AcuI overnight at 37° C. in a 250 µL reaction. After heat inactivation of AcuT, small aliquots (1, 2, 5, and 10 µL) were transformed into ER2502 and plated on ampicillin agar plates. Each transformation yielded 5–20 colonies after incubation at 37° C. overnight. Nine colonies from the partial library and nine colonies from the complete library were grown for 6 hrs and plasmid DNA was prepared. The eighteen clones were digested with 4 units of native AcuI to test for the presence of a functional AcuI methylase gene. Three clones were protected from AcuI digestion and thus potentially carried the AcuI methylase gene. These clones designated ANS3, ANS6 and ANS8 were sequenced with pUC19 primers s1233s and s1224s (New England Biolabs, (Beverly, Mass.)) to reveal a partial open reading frame with similarity to the eco57IM gene. Clone ANS6 was chosen for further characterization and the 2.8 kb gene insert was confirmed to encode the AcuI methylase gene (acuIM). The vector/insert junction revealed that clone ANS6 was isolated from the NlaIII partial library. Methylase clone ANS6 was completely sequenced by primer walking to define a 1608 bp ORF that encodes a protein of 535 amino acids.

2. Cloning of the AcuI Restriction Endonuclease Gene (acuIRM) by Inverse PCR.

An assumption was made that the AcuI R-M gene organization would be the same as the Eco57I R-M system. Therefore, inverse PCR was initially conducted downstream of the AcuI methylase gene in order to locate the AcuI endonuclease gene. Inverse PCR primers were designed to anneal to the end of insert ANS6. AcuI genomic DNA was digested with the following enzymes: AciI, AflIII, AluI, BsaAI, MfeI, MseI, RsaI, Sau3AI and Tsp45I. After self-ligation of the digestion products, inverse PCR was performed using 35 cycles. Inverse PCR products were obtained from all nine of the digestion/ligation reactions. The AflIII inverse PCR product (1.6 kb) was gel-purified and was partially sequenced. A BLAST search of this sequence indicated a high degree of similarity to the Acinetobacter ADP1 mismatch repair gene mutS. Therefore, it was concluded that acuIRM does not reside immediately downstream of acuIM.

Inverse PCR efforts were then redirected to the region upstream of acuIM. The first round of upstream inverse PCR (using 8 different digests) yielded products ranging from 0.4–1.8 kb. The complete 1.8 kb region was sequenced to reveal an incomplete open reading frame with high similarity to the Eco57I endonuclease gene. This partial ORF was then assumed to be acuIRM. As this gene was expected to be approximately 3.0 kb, a second round of inverse PCR was performed (using 8 different digests). Round two PCR products ranged from 0.6–2.0 kb. After multiple sequencing reactions, the beginning of acuIRM was found as an in-frame GTG was located immediately following a TAA stop codon. The GTG codon codes for valine and translation can be initiated at this codon when other essential genetic elements are present. Initially, the acuIRM ORF was defined as 2961 bp due to an erroneous sequence at the 3' end of the gene. Later, the corrected acuIRM ORF was confirmed to be 3003 bp.

3. Attempt to Over-Express acuIRM from pACYC-T7ter

The methylase clone ANS6 was transformed into T7 expression strain ER2744 to prepare pre-modified host cells. The initially defined acuIRM gene (2961 bp) was PCR-amplified from AcuI genomic DNA using a forward primer (291-043) with an NdeI site overlapping the GTG start to create an ATG start and a reverse primer (291-044) encoding a BamHI site downstream of the erroneous stop codon. A 3.0 kb PCR product was obtained using a Taq/Vent® polymerase mix (50:1 units, respectively). After NdeI/BamHI digestion and gel-purification, the fragment was ligated into NdeI/BamHI cut, CIP-treated pACYC-T7ter. This expression vector is derived from pACYC184 and is present at 5–8 copies in the cell (see U.S. Pat. No. 6,335,190). The ligation reaction was transformed into ER2744 [pUC19-AcuIM clone ANS6] by electroporation. Eighteen colonies were grown for plasmid DNA isolation and induction with IPTG. None of the induced cultures displayed AcuI endonuclease activity when cell extract was incubated with substrate pUC19. Failure to obtain an over-expressing clone may have been due to any of the following reasons: A) All eighteen clones may have contained detrimental mutations as a result of PCR amplification by Taq/Vent® polymerase. B) The low copy number of the expression vector results in an undetectable level of AcuI endonuclease. C) Unknown at the time, amplification with reverse primer 291-044 results in a modified gene product where the last five amino acids are altered.

4. Attempt to Over-Express acuIRM from pUC19-Kan

To increase the probability of isolating a recombinant AcuI clone, items A and B were addressed. First, the high-copy number vector pUC19-Kan was chosen for endonuclease expression. An additional benefit of employing a kanamycin vector is reduced loss of plasmid in late-log cultures as compared to ampicillin selection (see pET system manual, www.novagen.com) To address the potential problem of polymerase fidelity, PCR-amplification of the acuIRM ORF was attempted with Vent® and Deep Vent® (New England Biolabs (Beverly, Mass.)) with negative results. Consequently, the acuIRM ORF was amplified with a Taq/Vent® mix (as described previously) using forward primer 291-287 and reverse primer 291-044. Primer 291-287 contains a PstI site, a Shine-Delgarno sequence and an ATG start. After PstI digestion and gel-purification, the acuIRM PCR product was phosphorylated with T4 polynucleotide kinase. Next, the acuIRM gene was ligated into pUC19-Kan which had been prepared by PstI/HincII digestion, CIP treatment and gel-purification. The ligation reaction was transformed into ER2744 [pACYC184-AcuIM] by electroporation. The use of pUC19-Kan for endonuclease expression required that the acuIM gene be subcloned into pACYC184, a vector with a compatible origin of replication. (see description in section 5). Thirty-six pUC19-Kan colonies were grown to mid-log phase and cell extract was prepared. None of the extracts exhibited AcuI endonuclease activity when incubated with substrate pUC19.

To further address the issue of polymerase fidelity, KOD HiFi polymerase (Novagen (Madison, Wis.) product #71085-3) was used to amplify the acuIRM ORF with primers 291-287 and 291-044. The product was ligated into pUC19-Kan, transformed into ER2744 [pACYC184-AcuIM] and plated on LB-Kan,Cam plates. Thirty-six colonies were grown to mid-log phase and cell extract was prepared. Again, none of the extracts exhibited AcuI endonuclease activity when incubated with lambda DNA. The insert frequency of these thirty-six clones was analyzed by colony PCR and thirty-four of thirty-six clones appeared to contain acuIRM inserts. At this point, a decision was made to employ a third expression vector, pET28a(Kan$^R$).

5. Subcloning of acuIM from pUC19 (Clone ANS6) to pACYC184 and Preparation of an AcuI Over-Expression Host.

The acuIM containing insert of clone ANS6 is 2.8 kb. A SalI site is present near one end of the insert upstream from the acuIM start codon. A second SalI site is present within the pUC19 polylinker. Thus, SalI digestion was used to transfer a 2.8 kb acuIM fragment into pACYC184 prepared by SalI digestion and CIP treatment. The in vivo function of acuIM within pACYC184 was verified by digesting plasmid isolates with AcuI endonuclease. Several isolates displayed complete resistance to AcuI digestion and clone #9 was chosen for use in host cell pre-modification. Electrocompetent cells were prepared from clone #9 to create T7 expression host ER2744 [pACYC184-AcuIM].

6. Over-Expression of acuIRM from pET28a

T7 expression vector pET28a (Novagen (Madison, Wis.) product #69864-3) was prepared by NcoI/BamHI digestion followed by CIP treatment. KOD HiFi polymerase was used to PCR-amplify the acuIR gene using primers 291-287 and 291-044. After NcoI/BamHI digestion and gel-purification, the PCR product was ligated into pET28a (Kan$^R$). The ligation mix was transformed into ER2744 [pACYC184-AcuIM] by electroporation and plated on LB-Kan,Cam plates. Eighteen colonies were grown, induced for 3 hours with IPTG and cell extract was prepared. Fifteen of eighteen extracts produced a digestion pattern identical to native AcuI. Clone #28 was chosen for further characterization and sequencing. Sequencing results revealed a one-base deletion near the 3' end of the acuIRM gene as compared to a sequence derived from the original ANS6 clone. Re-evaluation of inverse PCR sequences and the ANS6 sequence led to the conclusion that the original ANS6 sequence had been misinterpreted and the acuIRM stop codon had been predicted incorrectly. As a result, the gene product from clone 28 is altered at the very C-terminus and yet maintains relatively normal specific activity. Since the sequence of clone 28 was otherwise wild-type, this clone was modified to correct the 3' end of the acuIRM gene sequence.

7. Modification of Clone 28 to Create Wild-Type acuIRM Clone #288

The 3' end of the acuIRM gene was corrected by transferring a 290 bp fragment from clone ANS6 into clone 28 to create pET28a-AcuIRM clone #288. A unique PmeI site is present 106 bp upstream from the correct acuIRM stop codon. In addition, an EcoRI site is present 184 bp downstream of the stop codon. Therefore, clone 28 and clone ANS6 were digested with PmeI/EcoRI and the appropriate fragments were gel-purified. (Note that the EcoRI site of clone 28 is present in the pET28a polylinker immediately downstream of the BamHI site initially used for cloning the acuIRM gene). The two fragments were ligated and transformed into ER2744 [pACYC184-AcuIM]. Nine colonies were grown to assay for the over-expression of AcuI. The extract of clone #288 exhibited the same level of AcuI activity as clone #28. Clone #288 was sequenced using the T7 terminator primer to verify that the 3' end was corrected to match the wild-type sequence.

The expression level of clone #288 was estimated by growing 500 mL of cells, inducing for 3 hours with 0.5 mM IPTG and preparing cell extract from the cell pellet. The yield of AcuI was estimated to be 17,400 units per gram of wet cells using lambda DNA as the substrate. The final AcuI over-production strain is *E. coli* strain ER2744 [pET28a-AcuIRM, pACYC184-AcuIM].

The present invention is further illustrated by the following Example. This Example is provided to aid in the understanding of the invention and is not construed as a limitation thereof.

The references cited above and below are herein incorporated by reference.

EXAMPLE I

Cloning of AcuI Restriction-Modification System in *E. coli*

1. Preparation of Genomic DNA

Genomic DNA is prepared from 7.8 g of *Acinetobacter calcoaceticus* SRW4 (NEB #1449, New England Biolabs strain collection) by the standard procedure consisting of the following steps:

a. Cell lysis by resuspending cells in 50 mM Tris-HCl (pH 8.0), 0.1 M EDTA and addition of lysozyme (2.8 mg/ml final conc.).

b. Further cell lysis by addition of SDS at a final concentration of 1.25%.

c. Further cell lysis by addition of Triton X-100 at a final concentration of 1.0%.

d. Addition of 25 ml TE (pH 8.0) and 40 ml distilled water to improve DNA yield during phenol-chloroform extraction.

e. After freezing overnight at −20° C., proteins are removed by phenol-chloroform extraction four times (equal volume) and chloroform extraction once (equal volume).

f. Dialysis in 4 liters of TE buffer, buffer change twice.

g. RNase A treatment to digest RNA (0.1 mg/ml final conc.).

h. Genomic DNA concentration was estimated to be 0.3 mg/ml so DNA precipitation is not necessary.

i. Genomic DNA yield was estimated to be 6 mg.

2. Restriction Digestion of Genomic DNA and Construction of Genomic DNA Libraries AcuI genomic DNA (9 μg per reaction) is completely digested with BamHI, EcoRI or SphI or partially digested with ApoI, Sau3AI or NlaIII. The partial digests are optimized to yield DNA fragments in the 2–10 kb range by using varying amounts of ApoI, Sau3AI and NlaIII restriction endonuclease in 30 min reactions. After gel purification of the six fragment types, each lot is ligated into vector pUC19. Vector pUC19 possesses two AcuI (Eco57I) sites, a necessary feature for the methylation selection procedure. The BamHI and Sau3AI fragments are ligated into BamHI cut, CIP-treated pUC19. The EcoRI and ApoI fragments are ligated into EcoRI cut, CIP-treated pUC19. And the SphI and NlaIII fragments are ligated into SphI cut, CIP-treated pUC19. The six ligation reactions are incubated overnight and then each is transformed into ER2502 by electroporation. (ER2502 is strain RR1, endA). Each ligation each yielded >30,000 colonies (except the BamHI ligation yielded only 18,000 colonies). An aliquot of each ligation is separately transformed into ER2683 to conduct blue/white screening to assess the number of insert-containing clones. The percentage of inserts in each library varied from 50–87% (except the BamHI assessment found only 1 of 13 white colonies). Therefore, the BamHI library was excluded. The "complete" library was created by inoculating approximately 10,000 colonies of each of the EcoRI and SphI libraries into 500 mL LB plus Amp, growing for 3 hours and isolating plasmid DNA by the Qiagen (Studio City, Calif.) Maxiprep procedure. The "partial" library was created in the same manner by pooling approximately 10,000 ApoI colonies, 10,000 NlaII colonies and 20,000 Sau3AI colonies.

3. Challenge of AcuI Vector Libraries to Isolate the AcuI Methylase Gene.

Each library (5 μg) is challenged with 20 units of native AcuI overnight at 37° C. in a 250 μL reaction. After heat inactivation of AcuI, small aliquots (1, 2, 5, and 10 μL) are transformed into ER2502 and plated on ampicillin agar plates. Each transformation yielded 5–20 colonies after incubation at 37° C. overnight. Nine colonies from the partial library and nine colonies from the complete library were grown for 6 hrs and plasmid DNA was prepared. The eighteen clones were digested with 4 units of native AcuI to test for the presence of a functional AcuI methylase gene.

Three clones were protected from AcuI digestion and thus potentially carried the AcuI methylase gene. These clones designated ANS3, ANS6 and ANS8 were sequenced with pUC19 primers s1233s and s1224s (New England Biolabs (Beverly, Mass.)) to reveal a partial open reading frame with similarity to the eco57IM gene. Clone ANS6 was chosen for further characterization and the 2.8 kb gene insert was confirmed to encode the AcuI methylase gene (acuIM). The vector/insert junction revealed that clone ANS6 was isolated from the NlaIII partial library. Methylase clone ANS6 was completely sequenced by primer walking to define a 1608 bp ORF that encodes a protein of 535 amino acids with high similarity to the amino-methyltransferase family.

4. Cloning of the AcuI Restriction Endonuclease Gene (acuIRM) by Inverse PCR.

Figure 2:
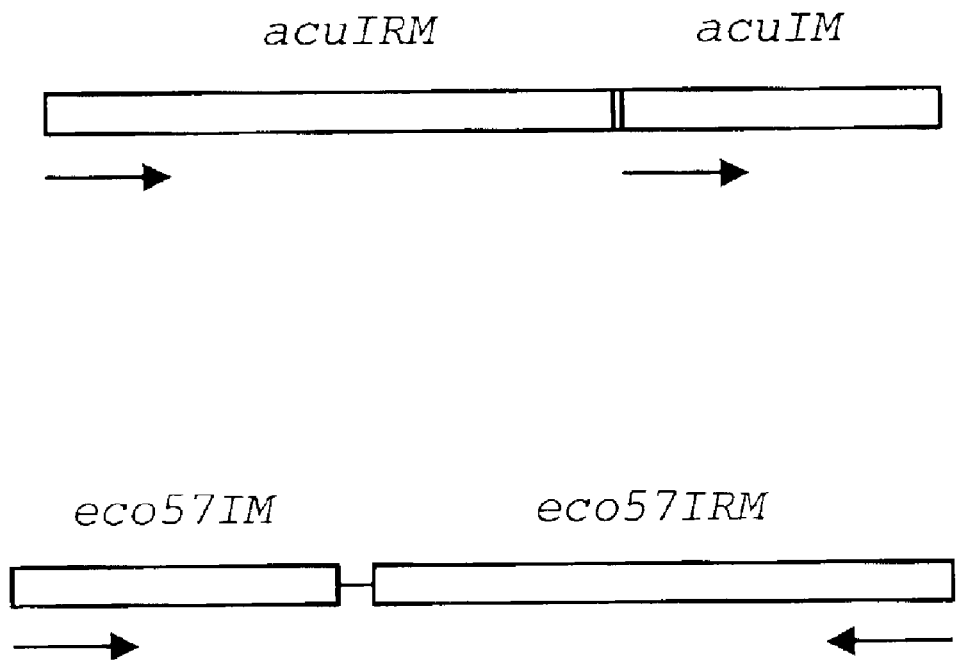
FIG. 2 Gene organization of the AcuI R-M system relative to the gene organization of the Eco57I R-M system. acuIRM, AcuI restriction endonuclease gene; acuIM, AcuI methylase gene; eco57IRM, Eco57I restriction endonuclease gene; eco57IM, Eco57I methylase gene FIG. 3 AcuI methylase gene sequence (SEQ ID NO:1) (acuIM, 1608 bp) and the encoded amino acid sequence (SEQ ID NO:2).

The acuIRM gene encoding the AcuI endonuclease-methylase fusion protein resides upstream of the acuIM gene. The AcuI gene organization differs from the Eco57I gene organization (see FIG. 2). Inverse PCR was conducted to characterize the genomic region upstream of acuIM. Inverse PCR primers 287-003 and 287-004 were designed to anneal upstream from the acuIM start codon. Round one inverse PCR primer sequences are as follows:

```
                                    (SEQ ID NO:5)
5' tataagctcttttttgcttggtcgc 3'     (287-003)

(SEQ ID NO:6)
5' aagagttctgaccccattgcaacg 3'      (287-004)
```

AcuI genomic DNA was digested with the following enzymes: AciI, ApoI, BsaAI, BstZ17I, DraI, HincII, NsiI and XmnI. After self-ligation of the digestion products (at 4 ng/μl), inverse PCR was performed using 35 cycles. Inverse PCR products were obtained from the following reactions: ApoI (0.8 kb), HincII (1.8 kb), XmnI (0.8 kb) and AciI (0.4 kb). The ApoI, HincII and XmnI inverse PCR products were gel-purified and sequenced with primers 287-003 and 287-004. The resulting 1.8 kb sequence revealed an incomplete open reading frame with high similarity to the Eco57I endonuclease-methylase fusion gene. This partial ORF was assumed to be acuIRM. As this gene was expected to be approximately 3.0 kb, a second round of inverse PCR was performed.

Round two inverse PCR primer sequences are as follows:

```
                                    (SEQ ID NO:7)
5' tacctgttggaattaattgagaag 3'      (288-109)

(SEQ ID NO:8)
5' tcggtacttataagctgtcttatg 3'      (288-110)
```

AcuI genomic DNA was digested with the following enzymes: AciI, Sau3AI, ApoI, DraI, TseI, SfcI, BclI and BsrBI. After self-ligation of the digestion products (at 4 ng/μl), inverse PCR was performed using 35 cycles. Round two PCR products ranged from 0.6–2.0 kb. A 1.0 kb fragment derived from the DraI digest and a 2.0 kb fragment derived from the TseI digest were gel-purified. Sequencing was carried out using primers 288-109, 288-110 and 288-277.

```
5' cccagagtaaacggactctcttcc 3'        (SEQ ID NO:9)
                                      (288-277)
```

The second round sequence revealed an in-frame GTG codon immediately following a TAA stop codon approximately 3 kb upstream of the acuIM gene. This GTG is the start of the acuIRM gene. Translation can be initiated at this valine codon when other essential genetic elements are present. The acuIRM ORF is 3003 bp, which encodes a protein of 1000 amino acids with a calculated molecular weight of 115,826 daltons.

5. Subcloning of the acuIM Gene into pACYC184

The acuIM containing insert of clone ANS6 is 2.8 kb. A SalI site is present near one end of the insert upstream from the acuIM start codon. A second SalI site is present within the pUC19 polylinker. Thus, SalI digestion was used to transfer a 2.8 kb acuIM fragment into pACYC184 prepared by SalI digestion and CIP treatment. The in vivo function of acuIM within pACYC184 was verified by digesting plasmid isolates with AcuI endonuclease. Several isolates displayed complete resistance to AcuI digestion and clone #9 was chosen for use in host cell pre-modification. The host cells used for AcuI over-expression were ER2744 [pACYC184-AcuIM].

6. Cloning of the 3003 bp ORF Upstream of acuIM to Confirm the Identity of acuIRM The gene product of the putative acuIRM ORF is 51% identical to the Eco57I restriction endonuclease. The identity and function of the acuIRM gene product was confirmed by cloning the gene into the *E. coli* T7 expression vector pET28a (Kan$^R$). Two PCR primers were synthesized for PCR amplification of the 3003 bp ORF from *Acinetobacter calcoaceticus* SRW4 genomic DNA:

```
5' ccaactgcaggaataacccatggttcatgatcataagcttgaa 3'  (SEQ ID NO:10)
(forward primer 291-287, underline = NcoI site)

5' ccttccggatccttaatataagggatcaagg 3'              (SEQ ID NO:11)
(reverse primer 291-044, underline = BamHI site)
```

PCR conditions were 94° C. for 2 min (1 cycle); 95° C. for 15 sec, 55° C. for 30 sec, 72° C. for 60 sec (18 cycles); 72° C. for 7 min (1 cycle). KOD HiFi polymerase (2 units) was used for PCR amplification. The PCR product was purified by Qiagen (Studio City, Calif.) spin column, digested with NcoI and BamHI at 37° C., purified by excision from a low-melt agarose gel and ligated to CIP treated pET28a with compatible ends. Following overnight ligation, the DNA was dialyzed against distilled water for 4 hours and transformed into ER2744 [pACYC184-AcuIM] by electroporation. The transformation mix was plated on LB-agar plus Kan, Cam. Eighteen colonies were grown (in 10 ml LB plus Kan/Cam), induced for 3 hours with 0.5 mM IPTG and cell extract was prepared by sonication. Fifteen of eighteen extracts produced a lambda digestion pattern identical to native AcuI. Clone #28 was chosen for further characterization and sequencing. Sequencing results revealed a one-base deletion near the 3' end of the acuIRM gene as compared to a sequence derived from the original ANS6 clone. Re-evaluation of inverse PCR sequences and the ANS6 sequence led to the conclusion that the original ANS6 sequence had been misinterpreted and the acuIRM stop codon had been predicted incorrectly. As a result, the gene product from clone 28 is altered at the very C-terminus and yet maintains relatively normal specific activity. Since the sequence of clone 28 was otherwise wild-type, this clone was modified to correct the 3' end of the acuIRM gene sequence.

7. Modification of Clone 28 to Create Wild-Type acuIRM Clone #288

The 3' end of the acuIRM gene was corrected by transferring a 290 bp fragment from clone ANS6 into clone 28 to create pET28a-AcuIRM clone #288. A unique PmeI site is present 106 bp upstream from the correct acuIRM stop codon. In addition, an EcoRI site is present 184 bp downstream of the stop codon. Therefore, clone 28 and clone ANS6 were digested with PmeI/EcoRI and the appropriate fragments were gel-purified. (Note that the EcoRI site of clone 28 is present in the pET28a polylinker immediately downstream of the BamHI site initially used for cloning the acuIRM gene). The two fragments were ligated and transformed into ER2744 [pACYC184-AcuIM]. Nine colonies were grown (in 10 ml LB plus Kan/Cam) to assay for the over-expression of AcuI. The extract of clone #288 exhibited the same level of AcuI activity as clone #28. Clone #288 was sequenced using the T7 terminator primer to verify that the 3' end was corrected to match the wild-type acuIRM sequence.

8. Design of Correct acuIRM Reverse Primer for Subsequent PCR Amplification

Any subsequent manipulation of the acuIRM gene requires a proper reverse PCR primer that anneals downstream of the stop codon. Primer 293-171 (listed below) allows for PCR amplification of the acuIRM gene from pET28a (clone #288) when paired with forward primer 291-287 using the same PCR conditions described in section 6.

```
5' ccttccggatccacgtaattttcggcagatgc 3'       (SEQ ID NO:12)
(reverse primer 293-171, underline = BamHI site)
```

9. Estimation of AcuI Yield

Figure 5:
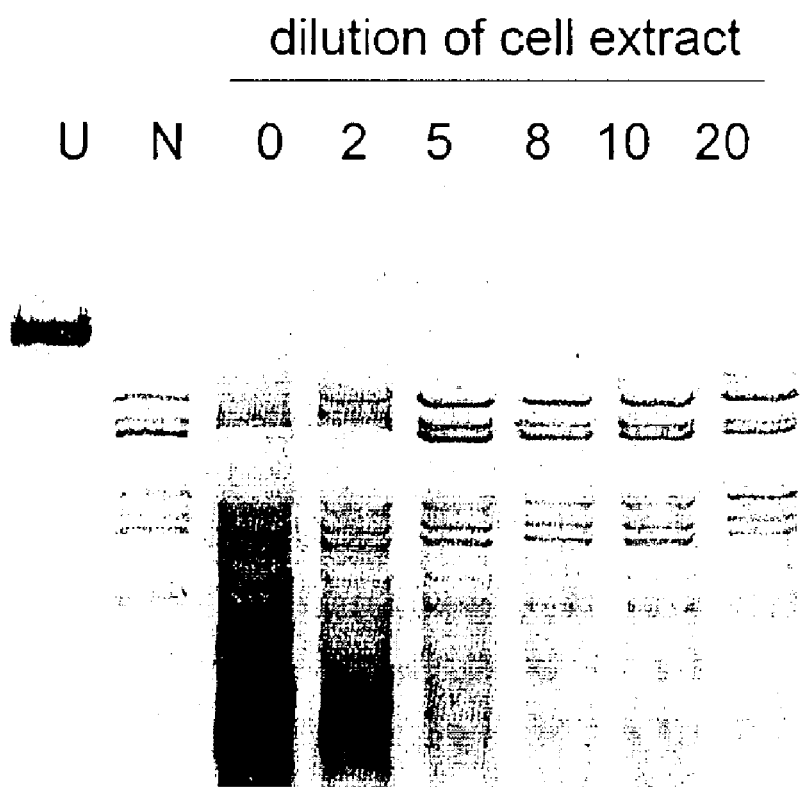
FIG. 5 Recombinant AcuI endonuclease activity in cell extract. (U) is undigested lambda substrate; (N) is digestion with 5 units native AcuI.

AcuI yield was estimated by growing clone #288 in LB plus Kan/Cam to late log phase, inducing for 3 hours with 0.5 mM IPTG and preparing cell extract from the cell pellet. The yield of recombinant AcuI was estimated to be 17,400 units per gram of wet cells using lambda DNA as the substrate (see FIG. 5). The AcuI over-production strain *E. coli* ER2744 [pET28a-AcuIRM, pACYC184-AcuIM] has been deposited under the terms and conditions of the Budapest Treaty with the American Type Culture Collection on Apr. 15, 2003 and received the Accession No. PTA-1513.

What is claimed is:

1. Isolated DNA encoding the AcuI restriction endonuclease, wherein the isolated DNA is obtainable from *Acinetobacter calcoaceticus* SRW4.

2. A recombinant DNA vector comprising a vector into which a DNA segment encoding the AcuI restriction endonuclease has been inserted.

3. Isolated DNA encoding the AcuI restriction endonuclease and AcuI methylase, wherein the isolated DNA is obtainable from ATCC No. PTA-1513.

4. A cloning vector that comprise the isolated DNA of claim 3.

5. A host cell transformed by the vector of claim 2 or 4.

6. A method of producing recombinant AcuI restriction endonuclease comprising culturing the host cell of claim 5 under conditions suitable for expression of said endonuclease and methylase.

* * * * *

SEQUENCE LISTING

<160> NUMBER OF SEQ ID NOS: 12

<210> SEQ ID NO 1
<211> LENGTH: 1608
<212> TYPE: DNA
<213> ORGANISM: Acinetobacter calcoaceticua SRW4 methylase gene
<220> FEATURE:
<221> NAME/KEY: CDS
<222> LOCATION: (1)..(1608)

<400> SEQUENCE: 1

| | | | | | | | | | | | | | | | | |
|---|---|---|---|---|---|---|---|---|---|---|---|---|---|---|---|---|
| atg | aag | ctc | att | aaa | gat | gca | tct | gcc | gaa | aaa | tta | cgt | ggc | ggg | ttt | 48 |
| Met | Lys | Leu | Ile | Lys | Asp | Ala | Ser | Ala | Glu | Lys | Leu | Arg | Gly | Gly | Phe | |
| 1 | | | | 5 | | | | | 10 | | | | | 15 | | |
| tat | aca | cct | gag | cca | att | gct | gca | ttt | att | cta | aaa | tgg | gga | ata | aat | 96 |
| Tyr | Thr | Pro | Glu | Pro | Ile | Ala | Ala | Phe | Ile | Leu | Lys | Trp | Gly | Ile | Asn | |
| | | | 20 | | | | | 25 | | | | | 30 | | | |
| ggt | agt | tct | gat | tat | gac | atc | tta | gaa | cca | agt | tgt | ggt | gat | ggt | gtg | 144 |
| Gly | Ser | Ser | Asp | Tyr | Asp | Ile | Leu | Glu | Pro | Ser | Cys | Gly | Asp | Gly | Val | |
| | | 35 | | | | | 40 | | | | | 45 | | | | |
| ttt | tta | gaa | caa | cta | aag | aag | aaa | gat | ttc | tgt | ttt | caa | tct | gtt | act | 192 |
| Phe | Leu | Glu | Gln | Leu | Lys | Lys | Lys | Asp | Phe | Cys | Phe | Gln | Ser | Val | Thr | |
| | 50 | | | | | 55 | | | | | 60 | | | | | |
| gct | atc | gaa | ttc | gat | act | att | gaa | gcg | aat | aaa | gcg | aac | caa | att | gat | 240 |
| Ala | Ile | Glu | Phe | Asp | Thr | Ile | Glu | Ala | Asn | Lys | Ala | Asn | Gln | Ile | Asp | |
| 65 | | | | | 70 | | | | | 75 | | | | | 80 | |
| att | gct | aat | aaa | aaa | gta | atc | aat | cag | gat | ttt | cat | tta | tat | tgt | aat | 288 |
| Ile | Ala | Asn | Lys | Lys | Val | Ile | Asn | Gln | Asp | Phe | His | Leu | Tyr | Cys | Asn | |
| | | | | 85 | | | | | 90 | | | | | 95 | | |
| aca | aca | tct | caa | aaa | ttt | gat | ctt | gta | gtc | ggt | aat | cct | cca | tat | att | 336 |
| Thr | Thr | Ser | Gln | Lys | Phe | Asp | Leu | Val | Val | Gly | Asn | Pro | Pro | Tyr | Ile | |
| | | | 100 | | | | | 105 | | | | | 110 | | | |
| cgt | tat | caa | tat | ttt | gat | aag | agt | caa | cag | att | gaa | gca | gat | aaa | ata | 384 |
| Arg | Tyr | Gln | Tyr | Phe | Asp | Lys | Ser | Gln | Gln | Ile | Glu | Ala | Asp | Lys | Ile | |
| | | 115 | | | | | 120 | | | | | 125 | | | | |
| ttt | aaa | aag | gct | ggg | tta | aaa | tat | tct | aaa | tta | aca | aat | gct | tgg | gta | 432 |
| Phe | Lys | Lys | Ala | Gly | Leu | Lys | Tyr | Ser | Lys | Leu | Thr | Asn | Ala | Trp | Val | |
| | 130 | | | | | 135 | | | | | 140 | | | | | |
| tca | ttt | att | gtt | ggt | tct | agt | tta | ttg | cta | aaa | gaa | aaa | ggc | aaa | ata | 480 |
| Ser | Phe | Ile | Val | Gly | Ser | Ser | Leu | Leu | Leu | Lys | Glu | Lys | Gly | Lys | Ile | |
| 145 | | | | | 150 | | | | | 155 | | | | | 160 | |
| ggt | ttt | gtt | gtt | cca | gca | gaa | ttg | ttg | caa | gta | tct | tac | gct | caa | cag | 528 |
| Gly | Phe | Val | Val | Pro | Ala | Glu | Leu | Leu | Gln | Val | Ser | Tyr | Ala | Gln | Gln | |
| | | | | 165 | | | | | 170 | | | | | 175 | | |
| ctc | cga | gaa | ttt | ttg | gca | cat | ttt | tac | aat | aaa | att | aat | att | att | tct | 576 |
| Leu | Arg | Glu | Phe | Leu | Ala | His | Phe | Tyr | Asn | Lys | Ile | Asn | Ile | Ile | Ser | |
| | | | 180 | | | | | 185 | | | | | 190 | | | |
| ttt | gaa | aaa | tta | gtt | ttt | cct | gat | att | cag | cag | gaa | gtc | gta | cta | cta | 624 |
| Phe | Glu | Lys | Leu | Val | Phe | Pro | Asp | Ile | Gln | Gln | Glu | Val | Val | Leu | Leu | |
| | | 195 | | | | | 200 | | | | | 205 | | | | |
| ttg | tgt | gaa | aag | aat | agt | gat | act | acc | cat | ttg | ata | gaa | cat | ctt | gaa | 672 |
| Leu | Cys | Glu | Lys | Asn | Ser | Asp | Thr | Thr | His | Leu | Ile | Glu | His | Leu | Glu | |
| | 210 | | | | | 215 | | | | | 220 | | | | | |
| tta | aaa | gat | gcc | tct | gat | ctt | gaa | aaa | ctg | gat | gtg | aac | ctt | tta | aag | 720 |
| Leu | Lys | Asp | Ala | Ser | Asp | Leu | Glu | Lys | Leu | Asp | Val | Asn | Leu | Leu | Lys | |
| 225 | | | | | 230 | | | | | 235 | | | | | 240 | |
| agt | cct | cgt | aaa | cag | att | gat | ttc | aaa | tct | aat | aaa | tgg | act | tat | tat | 768 |
| Ser | Pro | Arg | Lys | Gln | Ile | Asp | Phe | Lys | Ser | Asn | Lys | Trp | Thr | Tyr | Tyr | |
| | | | | 245 | | | | | 250 | | | | | 255 | | |

|  |  |  |  |  |  |  |  |  |  |  |  |  |  |  |  | |
|---|---|---|---|---|---|---|---|---|---|---|---|---|---|---|---|---|
| ttc | tta | gag | caa | gaa | gag | att | gat | ttt | ctt | gaa | aat | att | gct | gaa | aga | 816 |
| Phe | Leu | Glu | Gln | Glu | Glu | Ile | Asp | Phe | Leu | Glu | Asn | Ile | Ala | Glu | Arg | |
|  |  |  | 260 |  |  |  |  | 265 |  |  |  |  | 270 |  |  | |
| aaa | aat | att | cca | ata | tta | ggt | gat | ttt | gca | gat | gta | gaa | gta | gga | att | 864 |
| Lys | Asn | Ile | Pro | Ile | Leu | Gly | Asp | Phe | Ala | Asp | Val | Glu | Val | Gly | Ile | |
|  |  | 275 |  |  |  |  | 280 |  |  |  |  | 285 |  |  |  | |
| act | aca | gga | gca | aat | agc | tat | ttt | act | gtg | cct | att | tca | act | gta | aaa | 912 |
| Thr | Thr | Gly | Ala | Asn | Ser | Tyr | Phe | Thr | Val | Pro | Ile | Ser | Thr | Val | Lys | |
|  | 290 |  |  |  |  | 295 |  |  |  |  | 300 |  |  |  |  | |
| gaa | ttt | aat | ctt | gaa | caa | ttt | gct | aag | cct | atg | gtt | ggt | cgt | agt | gta | 960 |
| Glu | Phe | Asn | Leu | Glu | Gln | Phe | Ala | Lys | Pro | Met | Val | Gly | Arg | Ser | Val | |
| 305 |  |  |  |  | 310 |  |  |  |  | 315 |  |  |  |  | 320 | |
| caa | gtg | aac | agt | atc | acg | ttt | act | gag | agt | gac | tgg | tta | cag | aac | tta | 1008 |
| Gln | Val | Asn | Ser | Ile | Thr | Phe | Thr | Glu | Ser | Asp | Trp | Leu | Gln | Asn | Leu | |
|  |  |  |  | 325 |  |  |  |  | 330 |  |  |  |  | 335 |  | |
| caa | atg | gaa | gca | aaa | gca | aat | tta | ttg | gtt | ttc | cca | aat | cgt | aat | caa | 1056 |
| Gln | Met | Glu | Ala | Lys | Ala | Asn | Leu | Leu | Val | Phe | Pro | Asn | Arg | Asn | Gln | |
|  |  |  | 340 |  |  |  |  | 345 |  |  |  |  | 350 |  |  | |
| att | tct | aat | cat | agt | ggt | gcg | aat | aaa | tat | att | gaa | tat | ggt | gaa | gaa | 1104 |
| Ile | Ser | Asn | His | Ser | Gly | Ala | Asn | Lys | Tyr | Ile | Glu | Tyr | Gly | Glu | Glu | |
|  |  | 355 |  |  |  |  | 360 |  |  |  |  | 365 |  |  |  | |
| ctg | gga | gtt | aac | aag | gga | tat | aag | aca | cgt | att | cgt | gat | gac | tgg | ttt | 1152 |
| Leu | Gly | Val | Asn | Lys | Gly | Tyr | Lys | Thr | Arg | Ile | Arg | Asp | Asp | Trp | Phe | |
| 370 |  |  |  |  | 375 |  |  |  |  | 380 |  |  |  |  |  | |
| gtt | att | cca | tct | att | aag | ttg | tca | gac | gct | ttg | ttt | att | cgt | aga | aat | 1200 |
| Val | Ile | Pro | Ser | Ile | Lys | Leu | Ser | Asp | Ala | Leu | Phe | Ile | Arg | Arg | Asn | |
| 385 |  |  |  |  | 390 |  |  |  |  | 395 |  |  |  |  | 400 | |
| aac | ctg | ttc | cca | cga | ctt | att | ttg | aat | gaa | gcc | caa | gca | tat | aca | aca | 1248 |
| Asn | Leu | Phe | Pro | Arg | Leu | Ile | Leu | Asn | Glu | Ala | Gln | Ala | Tyr | Thr | Thr | |
|  |  |  |  | 405 |  |  |  |  | 410 |  |  |  |  | 415 |  | |
| gat | acg | atg | cat | cga | gtt | ttt | att | aaa | cag | gaa | act | aat | aag | cag | gct | 1296 |
| Asp | Thr | Met | His | Arg | Val | Phe | Ile | Lys | Gln | Glu | Thr | Asn | Lys | Gln | Ala | |
|  |  |  | 420 |  |  |  |  | 425 |  |  |  |  | 430 |  |  | |
| ttt | att | gct | agc | ttt | tat | aat | tct | tta | tct | tta | gcc | ttt | tct | gag | att | 1344 |
| Phe | Ile | Ala | Ser | Phe | Tyr | Asn | Ser | Leu | Ser | Leu | Ala | Phe | Ser | Glu | Ile | |
|  |  | 435 |  |  |  |  | 440 |  |  |  |  | 445 |  |  |  | |
| gtt | ggt | cgt | agc | tat | ggt | ggt | ggt | gtc | ttg | gaa | tta | atg | ccg | agt | gaa | 1392 |
| Val | Gly | Arg | Ser | Tyr | Gly | Gly | Gly | Val | Leu | Glu | Leu | Met | Pro | Ser | Glu | |
|  | 450 |  |  |  |  | 455 |  |  |  |  | 460 |  |  |  |  | |
| gca | gca | aga | att | tta | cta | cct | tat | caa | gtt | gat | aat | gat | aag | ttg | ttg | 1440 |
| Ala | Ala | Arg | Ile | Leu | Leu | Pro | Tyr | Gln | Val | Asp | Asn | Asp | Lys | Leu | Leu | |
| 465 |  |  |  | 470 |  |  |  |  | 475 |  |  |  |  | 480 |  | |
| gat | cag | att | gat | aaa | tta | atg | cgt | gaa | aaa | aga | agt | att | gat | gat | atc | 1488 |
| Asp | Gln | Ile | Asp | Lys | Leu | Met | Arg | Glu | Lys | Arg | Ser | Ile | Asp | Asp | Ile | |
|  |  |  |  | 485 |  |  |  |  | 490 |  |  |  |  | 495 |  | |
| tta | cat | att | tct | aat | gat | att | att | ctt | cga | caa | gca | tat | ggt | ttt | tca | 1536 |
| Leu | His | Ile | Ser | Asn | Asp | Ile | Ile | Leu | Arg | Gln | Ala | Tyr | Gly | Phe | Ser | |
|  |  |  | 500 |  |  |  |  | 505 |  |  |  |  | 510 |  |  | |
| aaa | aaa | gaa | att | gaa | ctt | gca | gat | cga | att | tgg | aag | aaa | tta | tct | gca | 1584 |
| Lys | Lys | Glu | Ile | Glu | Leu | Ala | Asp | Arg | Ile | Trp | Lys | Lys | Leu | Ser | Ala | |
|  |  | 515 |  |  |  |  | 520 |  |  |  |  | 525 |  |  |  | |
| agg | aga | ttg | aat | agg | ggg | aaa | taa |  |  |  |  |  |  |  |  | 1608 |
| Arg | Arg | Leu | Asn | Arg | Gly | Lys |  |  |  |  |  |  |  |  |  | |
| 530 |  |  |  | 535 |  |  |  |  |  |  |  |  |  |  |  | |

<210> SEQ ID NO 2
<211> LENGTH: 535
<212> TYPE: PRT
<213> ORGANISM: Acinetobacter calcoaceticua SRW4 methylase gene

<400> SEQUENCE: 2

```
Met Lys Leu Ile Lys Asp Ala Ser Ala Glu Lys Leu Arg Gly Gly Phe
 1               5                  10                  15
Tyr Thr Pro Glu Pro Ile Ala Ala Phe Ile Leu Lys Trp Gly Ile Asn
                20                  25                  30
Gly Ser Ser Asp Tyr Asp Ile Leu Glu Pro Ser Cys Gly Asp Gly Val
            35                  40                  45
Phe Leu Glu Gln Leu Lys Lys Lys Asp Phe Cys Phe Gln Ser Val Thr
    50                  55                  60
Ala Ile Glu Phe Asp Thr Ile Glu Ala Asn Lys Ala Asn Gln Ile Asp
65                  70                  75                  80
Ile Ala Asn Lys Lys Val Ile Asn Gln Asp Phe His Leu Tyr Cys Asn
                85                  90                  95
Thr Thr Ser Gln Lys Phe Asp Leu Val Val Gly Asn Pro Pro Tyr Ile
                100                 105                 110
Arg Tyr Gln Tyr Phe Asp Lys Ser Gln Gln Ile Glu Ala Asp Lys Ile
            115                 120                 125
Phe Lys Lys Ala Gly Leu Lys Tyr Ser Lys Leu Thr Asn Ala Trp Val
    130                 135                 140
Ser Phe Ile Val Gly Ser Ser Leu Leu Lys Glu Lys Gly Lys Ile
145                 150                 155                 160
Gly Phe Val Val Pro Ala Glu Leu Leu Gln Val Ser Tyr Ala Gln Gln
                165                 170                 175
Leu Arg Glu Phe Leu Ala His Phe Tyr Asn Lys Ile Asn Ile Ile Ser
            180                 185                 190
Phe Glu Lys Leu Val Phe Pro Asp Ile Gln Gln Glu Val Val Leu Leu
    195                 200                 205
Leu Cys Glu Lys Asn Ser Asp Thr Thr His Leu Ile Glu His Leu Glu
210                 215                 220
Leu Lys Asp Ala Ser Asp Leu Glu Lys Leu Asp Val Asn Leu Leu Lys
225                 230                 235                 240
Ser Pro Arg Lys Gln Ile Asp Phe Lys Ser Asn Lys Trp Thr Tyr Tyr
                245                 250                 255
Phe Leu Glu Gln Glu Glu Ile Asp Phe Leu Glu Asn Ile Ala Glu Arg
            260                 265                 270
Lys Asn Ile Pro Ile Leu Gly Asp Phe Ala Asp Val Glu Val Gly Ile
    275                 280                 285
Thr Thr Gly Ala Asn Ser Tyr Phe Thr Val Pro Ile Ser Thr Val Lys
290                 295                 300
Glu Phe Asn Leu Glu Gln Phe Ala Lys Pro Met Val Gly Arg Ser Val
305                 310                 315                 320
Gln Val Asn Ser Ile Thr Phe Thr Glu Ser Asp Trp Leu Gln Asn Leu
                325                 330                 335
Gln Met Glu Ala Lys Ala Asn Leu Leu Val Phe Pro Asn Arg Asn Gln
            340                 345                 350
Ile Ser Asn His Ser Gly Ala Asn Lys Tyr Ile Glu Tyr Gly Glu Glu
    355                 360                 365
Leu Gly Val Asn Lys Gly Tyr Lys Thr Arg Ile Arg Asp Asp Trp Phe
370                 375                 380
Val Ile Pro Ser Ile Lys Leu Ser Asp Ala Leu Phe Ile Arg Arg Asn
385                 390                 395                 400
Asn Leu Phe Pro Arg Leu Ile Leu Asn Glu Ala Gln Ala Tyr Thr Thr
                405                 410                 415
```

-continued

```
Asp Thr Met His Arg Val Phe Ile Lys Gln Glu Thr Asn Lys Gln Ala
            420                 425                 430

Phe Ile Ala Ser Phe Tyr Asn Ser Leu Ser Leu Ala Phe Ser Glu Ile
        435                 440                 445

Val Gly Arg Ser Tyr Gly Gly Val Leu Glu Leu Met Pro Ser Glu
    450                 455                 460

Ala Ala Arg Ile Leu Leu Pro Tyr Gln Val Asp Asn Asp Lys Leu Leu
465                 470                 475                 480

Asp Gln Ile Asp Lys Leu Met Arg Glu Lys Arg Ser Ile Asp Asp Ile
                485                 490                 495

Leu His Ile Ser Asn Asp Ile Ile Leu Arg Gln Ala Tyr Gly Phe Ser
            500                 505                 510

Lys Lys Glu Ile Glu Leu Ala Asp Arg Ile Trp Lys Lys Leu Ser Ala
        515                 520                 525

Arg Arg Leu Asn Arg Gly Lys
    530                 535
```

<210> SEQ ID NO 3
<211> LENGTH: 3003
<212> TYPE: DNA
<213> ORGANISM: Acinetobacter calcoaceticua SRW4 endonuclease gene
<220> FEATURE:
<221> NAME/KEY: CDS
<222> LOCATION: (1)..(3003)

<400> SEQUENCE: 3

```
gtg gtt cat gat cat aag ctt gaa tta gcc aaa ctt att cgc aac tat      48
Val Val His Asp His Lys Leu Glu Leu Ala Lys Leu Ile Arg Asn Tyr
1               5                  10                  15 gag acg aat aga aaa gaa tgt cta aat tct aga tat aat gaa aca ctt      96
Glu Thr Asn Arg Lys Glu Cys Leu Asn Ser Arg Tyr Asn Glu Thr Leu
            20                  25                  30 tta cga agt gat tat ctt gat cca ttt ttt gaa ctt ctt ggc tgg gat     144
Leu Arg Ser Asp Tyr Leu Asp Pro Phe Phe Glu Leu Leu Gly Trp Asp
        35                  40                  45 att aaa aat aaa gct gga aaa ccg act aat gaa aga gag gtt gtc ttg     192
Ile Lys Asn Lys Ala Gly Lys Pro Thr Asn Glu Arg Glu Val Val Leu
    50                  55                  60 gaa gag gca ctt aaa gca agt gca tct gaa cat tct aaa aaa cca gat     240
Glu Glu Ala Leu Lys Ala Ser Ala Ser Glu His Ser Lys Lys Pro Asp
65                  70                  75                  80 tat aca ttc aga ctt ttt tct gaa aga aag ttt ttc ttg gaa gct aaa     288
Tyr Thr Phe Arg Leu Phe Ser Glu Arg Lys Phe Phe Leu Glu Ala Lys
                85                  90                  95 aaa cca tca gtt cat att gaa tcg gat aat gaa act gct aaa caa gtg     336
Lys Pro Ser Val His Ile Glu Ser Asp Asn Glu Thr Ala Lys Gln Val
            100                 105                 110 cga aga tat ggc ttt acc gcc aaa cta aaa att tca gtt tta tca aat     384
Arg Arg Tyr Gly Phe Thr Ala Lys Leu Lys Ile Ser Val Leu Ser Asn
        115                 120                 125 ttt gaa tat tta gtt att tat gat acc tct gta aag gtt gat ggt gat     432
Phe Glu Tyr Leu Val Ile Tyr Asp Thr Ser Val Lys Val Asp Gly Asp
    130                 135                 140 gat acc ttt aat aag gca cgt ata aaa aaa tac cat tac aca gag tat     480
Asp Thr Phe Asn Lys Ala Arg Ile Lys Lys Tyr His Tyr Thr Glu Tyr
145                 150                 155                 160 gaa act cac ttt gat gaa att tgt gac tta tta gga aga gag tcc gtt     528
Glu Thr His Phe Asp Glu Ile Cys Asp Leu Leu Gly Arg Glu Ser Val
                165                 170                 175
```

-continued

| | | |
|---|---|---|
| tac tct ggg aat ttt gat aaa gaa tgg ttg agt atc gaa aat aaa att<br>Tyr Ser Gly Asn Phe Asp Lys Glu Trp Leu Ser Ile Glu Asn Lys Ile<br>           180                    185                    190 | 576 |
| aat cac ttt tct gta gat acc tta ttt tta aaa cag att aat aca tgg<br>Asn His Phe Ser Val Asp Thr Leu Phe Leu Lys Gln Ile Asn Thr Trp<br>           195                    200                    205 | 624 |
| cgt cta ttg ctt ggt gaa gaa atc tat aag tat caa cct acg ata caa<br>Arg Leu Leu Leu Gly Glu Glu Ile Tyr Lys Tyr Gln Pro Thr Ile Gln<br>210                    215                    220 | 672 |
| gag aat gag ctt aat gac att gta cag agc tat ctg aat aga att att<br>Glu Asn Glu Leu Asn Asp Ile Val Gln Ser Tyr Leu Asn Arg Ile Ile<br>225                    230                    235                    240 | 720 |
| ttt ttg aga gtc tgt gaa gat aga aat tta gag act tat cag aca tta<br>Phe Leu Arg Val Cys Glu Asp Arg Asn Leu Glu Thr Tyr Gln Thr Leu<br>                    245                    250                    255 | 768 |
| ctg aat ttt gct tca agt aat gat ttc tcc gct ctt att gat aag ttt<br>Leu Asn Phe Ala Ser Ser Asn Asp Phe Ser Ala Leu Ile Asp Lys Phe<br>           260                    265                    270 | 816 |
| aag cag gca gat cgt tgc tat aat tca ggc cta ttt gat caa ttg ctt<br>Lys Gln Ala Asp Arg Cys Tyr Asn Ser Gly Leu Phe Asp Gln Leu Leu<br>275                    280                    285 | 864 |
| aca gag caa att att gag gat att agt tct gta ttt tgg gta atc att<br>Thr Glu Gln Ile Ile Glu Asp Ile Ser Ser Val Phe Trp Val Ile Ile<br>           290                    295                    300 | 912 |
| aag caa tta tat tat cca gaa agt cct tat tca ttt agt gtg ttc tct<br>Lys Gln Leu Tyr Tyr Pro Glu Ser Pro Tyr Ser Phe Ser Val Phe Ser<br>305                    310                    315                    320 | 960 |
| tcg gat att tta ggt aat att tac gaa ata ttt tta tct gag aaa tta<br>Ser Asp Ile Leu Gly Asn Ile Tyr Glu Ile Phe Leu Ser Glu Lys Leu<br>                    325                    330                    335 | 1008 |
| gta att aat caa agc aga gtt gag tta gtc aag aaa cca gag aat tta<br>Val Ile Asn Gln Ser Arg Val Glu Leu Val Lys Lys Pro Glu Asn Leu<br>           340                    345                    350 | 1056 |
| gat aga gac att gtc aca aca cca acc ttt att att aat gac atc ttg<br>Asp Arg Asp Ile Val Thr Thr Pro Thr Phe Ile Ile Asn Asp Ile Leu<br>355                    360                    365 | 1104 |
| aga aat acg gtt cta ccg aag tgc tat gga aaa aca gat ata gaa att<br>Arg Asn Thr Val Leu Pro Lys Cys Tyr Gly Lys Thr Asp Ile Glu Ile<br>           370                    375                    380 | 1152 |
| cta cag cta aaa ttt gct gat att gct tgt ggt tcg gga gca ttt tta<br>Leu Gln Leu Lys Phe Ala Asp Ile Ala Cys Gly Ser Gly Ala Phe Leu<br>385                    390                    395                    400 | 1200 |
| ctg gag ttg ttc caa tta ctt aat gat act cta gtt gac tat tat tta<br>Leu Glu Leu Phe Gln Leu Leu Asn Asp Thr Leu Val Asp Tyr Tyr Leu<br>                    405                    410                    415 | 1248 |
| agt agt gat act tct caa tta att cca aca ggt atc ggt act tat aag<br>Ser Ser Asp Thr Ser Gln Leu Ile Pro Thr Gly Ile Gly Thr Tyr Lys<br>           420                    425                    430 | 1296 |
| ctg tct tat gaa atc aag aga aag gtt cta tta agt tgt att ttt ggc<br>Leu Ser Tyr Glu Ile Lys Arg Lys Val Leu Leu Ser Cys Ile Phe Gly<br>435                    440                    445 | 1344 |
| ata gat aag gac tta aat gct gta gag gct gca aag ttc gga ttg ttg<br>Ile Asp Lys Asp Leu Asn Ala Val Glu Ala Ala Lys Phe Gly Leu Leu<br>           450                    455                    460 | 1392 |
| cta aaa tta tta gag ggt gaa gac gta caa tct ata gct aat att aga<br>Leu Lys Leu Leu Glu Gly Glu Asp Val Gln Ser Ile Ala Asn Ile Arg<br>465                    470                    475                    480 | 1440 |
| cca gtt ctc cca gat tta tta gat aac ata ctt ttt ggt aac agt tta<br>Pro Val Leu Pro Asp Leu Leu Asp Asn Ile Leu Phe Gly Asn Ser Leu<br>                    485                    490                    495 | 1488 |

-continued

| | | |
|---|---|---|
| tta gaa cca gaa aaa gtc gag ctt gat cat cag gta gaa gta aat ccg<br>Leu Glu Pro Glu Lys Val Glu Leu Asp His Gln Val Glu Val Asn Pro<br>500 505 510 | 1536 |
| tta gat ttt tct gat tta aag ttt gat gta att gtt ggc aac cct cca<br>Leu Asp Phe Ser Asp Leu Lys Phe Asp Val Ile Val Gly Asn Pro Pro<br>515 520 525 | 1584 |
| tat atg aaa tca gag gat atg aag aat att act cct ttg gag tta cct<br>Tyr Met Lys Ser Glu Asp Met Lys Asn Ile Thr Pro Leu Glu Leu Pro<br>530 535 540 | 1632 |
| tta tat aag aaa aac tat gtt tct gct tat aag caa ttt gat aaa tat<br>Leu Tyr Lys Lys Asn Tyr Val Ser Ala Tyr Lys Gln Phe Asp Lys Tyr<br>545 550 555 560 | 1680 |
| ttc ttg ttc tta gag cgg ggt tta gct cta tta aaa gaa gag gga ata<br>Phe Leu Phe Leu Glu Arg Gly Leu Ala Leu Leu Lys Glu Glu Gly Ile<br>565 570 575 | 1728 |
| ctt gga tat att gtt cca agt aaa ttt act aaa gtg ggt gca ggg aaa<br>Leu Gly Tyr Ile Val Pro Ser Lys Phe Thr Lys Val Gly Ala Gly Lys<br>580 585 590 | 1776 |
| aag tta cgg gaa tta cta aca gat aag ggt tat ctt gac tct att gtt<br>Lys Leu Arg Glu Leu Leu Thr Asp Lys Gly Tyr Leu Asp Ser Ile Val<br>595 600 605 | 1824 |
| tct ttt ggt gct aat caa ata ttt cag gat aaa aca act tat act tgt<br>Ser Phe Gly Ala Asn Gln Ile Phe Gln Asp Lys Thr Thr Tyr Thr Cys<br>610 615 620 | 1872 |
| tta ctt att tta aga aaa act cct cat act gat ttt aaa tat gca gag<br>Leu Leu Ile Leu Arg Lys Thr Pro His Thr Asp Phe Lys Tyr Ala Glu<br>625 630 635 640 | 1920 |
| gtt cgt aat tta att gac tgg aaa gtg cgt aaa gct gat gct atg gaa<br>Val Arg Asn Leu Ile Asp Trp Lys Val Arg Lys Ala Asp Ala Met Glu<br>645 650 655 | 1968 |
| ttt tcc tct caa caa ctg agt aca ttg caa agt gat gcg tgg att tta<br>Phe Ser Ser Gln Gln Leu Ser Thr Leu Gln Ser Asp Ala Trp Ile Leu<br>660 665 670 | 2016 |
| att cca tct gaa tta atc tca gtt tat cat cag ata tta gca caa agc<br>Ile Pro Ser Glu Leu Ile Ser Val Tyr His Gln Ile Leu Ala Gln Ser<br>675 680 685 | 2064 |
| caa aag cta gag gat att gtc ggt att gat aat ata ttt aat ggg att<br>Gln Lys Leu Glu Asp Ile Val Gly Ile Asp Asn Ile Phe Asn Gly Ile<br>690 695 700 | 2112 |
| caa acc agt gct aat gat gtc tat att ttt gtg cca act cat gag gat<br>Gln Thr Ser Ala Asn Asp Val Tyr Ile Phe Val Pro Thr His Glu Asp<br>705 710 715 720 | 2160 |
| act gaa aac tat tat ttt ata aag aaa gga caa gag tac aaa att gaa<br>Thr Glu Asn Tyr Tyr Phe Ile Lys Lys Gly Gln Glu Tyr Lys Ile Glu<br>725 730 735 | 2208 |
| aag gaa att acg aag cct tat ttt aaa aca acg agt ggt gag gat aac<br>Lys Glu Ile Thr Lys Pro Tyr Phe Lys Thr Thr Ser Gly Glu Asp Asn<br>740 745 750 | 2256 |
| tta tat act tac cgt act ttc aag cct aat gct cga gtc att tat ccg<br>Leu Tyr Thr Tyr Arg Thr Phe Lys Pro Asn Ala Arg Val Ile Tyr Pro<br>755 760 765 | 2304 |
| tat act caa act gag agt agt gta gaa cta att cct tta gat gaa ata<br>Tyr Thr Gln Thr Glu Ser Ser Val Glu Leu Ile Pro Leu Asp Glu Ile<br>770 775 780 | 2352 |
| cga gaa att ttt cct tta gca tac aaa tat tta atg tcg ctt aag ttc<br>Arg Glu Ile Phe Pro Leu Ala Tyr Lys Tyr Leu Met Ser Leu Lys Phe<br>785 790 795 800 | 2400 |
| gtt tta agt agc ccc aaa cga gat ata aaa cct aga cct aaa aca aca<br>Val Leu Ser Ser Pro Lys Arg Asp Ile Lys Pro Arg Pro Lys Thr Thr<br>805 810 815 | 2448 |

-continued

| | | |
|---|---|---|
| aat gaa tgg cat agg tat gga cgg cat caa agt cta gat aat tgt ggg<br>Asn Glu Trp His Arg Tyr Gly Arg His Gln Ser Leu Asp Asn Cys Gly<br>820                          825                    830 | | 2496 |

```
aat gaa tgg cat agg tat gga cgg cat caa agt cta gat aat tgt ggg     2496
Asn Glu Trp His Arg Tyr Gly Arg His Gln Ser Leu Asp Asn Cys Gly
            820                 825                 830 ttg agt cag aaa att att gta ggt gtg ctt tca gtt ggt gat aag tac     2544
Leu Ser Gln Lys Ile Ile Val Gly Val Leu Ser Val Gly Asp Lys Tyr
        835                 840                 845 gct ata gat act tat gga acg ttg att tca tca ggc ggt acg gct gga     2592
Ala Ile Asp Thr Tyr Gly Thr Leu Ile Ser Ser Gly Gly Thr Ala Gly
    850                 855                 860 tac tgt gtg gtt gct ctt cca gat gat tgt aaa tat tca att tat tat     2640
Tyr Cys Val Val Ala Leu Pro Asp Asp Cys Lys Tyr Ser Ile Tyr Tyr
865                 870                 875                 880 tta cag gca att tta aac tca aaa tat tta gag tgg ttt agt gcc tta     2688
Leu Gln Ala Ile Leu Asn Ser Lys Tyr Leu Glu Trp Phe Ser Ala Leu
                885                 890                 895 cat gga gaa gtt ttc cga ggt ggt tat att gct agg gga act aag gtg     2736
His Gly Glu Val Phe Arg Gly Gly Tyr Ile Ala Arg Gly Thr Lys Val
            900                 905                 910 ctt aag aac ttg cct att agg aaa att gat ttt gat aat ctt gaa gaa     2784
Leu Lys Asn Leu Pro Ile Arg Lys Ile Asp Phe Asp Asn Leu Glu Glu
        915                 920                 925 gca aat cta cat gat cta att gcg acc aag caa aaa gag ctt ata gag     2832
Ala Asn Leu His Asp Leu Ile Ala Thr Lys Gln Lys Glu Leu Ile Glu
    930                 935                 940 att tat gac aaa ata gat gtt aat gta aat aat aaa aga gtt ctg acc     2880
Ile Tyr Asp Lys Ile Asp Val Asn Val Asn Asn Lys Arg Val Leu Thr
945                 950                 955                 960 cca ttg caa cgt atg ttt aaa cga gag aaa gag gtt tta gac caa ttg     2928
Pro Leu Gln Arg Met Phe Lys Arg Glu Lys Glu Val Leu Asp Gln Leu
                965                 970                 975 ttg agt cga ctg tat aac tta ggt gta gat gat tcc ttg atc cct tat     2976
Leu Ser Arg Leu Tyr Asn Leu Gly Val Asp Asp Ser Leu Ile Pro Tyr
            980                 985                 990 att aag gat ttg tat gaa gct cat  taa                                3003
Ile Lys Asp Leu Tyr Glu Ala His
        995                 1000
```

<210> SEQ ID NO 4
<211> LENGTH: 1000
<212> TYPE: PRT
<213> ORGANISM: Acinetobacter calcoaceticua SRW4 endonuclease gene

<400> SEQUENCE: 4

```
Val Val His Asp His Lys Leu Glu Leu Ala Lys Leu Ile Arg Asn Tyr
1               5                   10                  15

Glu Thr Asn Arg Lys Glu Cys Leu Asn Ser Arg Tyr Asn Glu Thr Leu
            20                  25                  30

Leu Arg Ser Asp Tyr Leu Asp Pro Phe Phe Glu Leu Leu Gly Trp Asp
        35                  40                  45

Ile Lys Asn Lys Ala Gly Lys Pro Thr Asn Glu Arg Glu Val Val Leu
    50                  55                  60

Glu Glu Ala Leu Lys Ala Ser Ala Ser Glu His Ser Lys Lys Pro Asp
65                  70                  75                  80

Tyr Thr Phe Arg Leu Phe Ser Glu Arg Lys Phe Phe Leu Glu Ala Lys
                85                  90                  95

Lys Pro Ser Val His Ile Glu Ser Asp Asn Glu Thr Ala Lys Gln Val
            100                 105                 110

Arg Arg Tyr Gly Phe Thr Ala Lys Leu Lys Ile Ser Val Leu Ser Asn
        115                 120                 125
```

-continued

Phe Glu Tyr Leu Val Ile Tyr Asp Thr Ser Val Lys Val Asp Gly Asp
130                 135                 140

Asp Thr Phe Asn Lys Ala Arg Ile Lys Lys Tyr His Tyr Thr Glu Tyr
145                 150                 155                 160

Glu Thr His Phe Asp Glu Ile Cys Asp Leu Leu Gly Arg Glu Ser Val
                165                 170                 175

Tyr Ser Gly Asn Phe Asp Lys Glu Trp Leu Ser Ile Glu Asn Lys Ile
            180                 185                 190

Asn His Phe Ser Val Asp Thr Leu Phe Leu Lys Gln Ile Asn Thr Trp
        195                 200                 205

Arg Leu Leu Leu Gly Glu Glu Ile Tyr Lys Tyr Gln Pro Thr Ile Gln
    210                 215                 220

Glu Asn Glu Leu Asn Asp Ile Val Gln Ser Tyr Leu Asn Arg Ile Ile
225                 230                 235                 240

Phe Leu Arg Val Cys Glu Asp Arg Asn Leu Glu Thr Tyr Gln Thr Leu
                245                 250                 255

Leu Asn Phe Ala Ser Ser Asn Asp Phe Ser Ala Leu Ile Asp Lys Phe
            260                 265                 270

Lys Gln Ala Asp Arg Cys Tyr Asn Ser Gly Leu Phe Asp Gln Leu Leu
        275                 280                 285

Thr Glu Gln Ile Ile Glu Asp Ile Ser Ser Val Phe Trp Val Ile Ile
    290                 295                 300

Lys Gln Leu Tyr Tyr Pro Glu Ser Pro Tyr Ser Phe Ser Val Phe Ser
305                 310                 315                 320

Ser Asp Ile Leu Gly Asn Ile Tyr Glu Ile Phe Leu Ser Glu Lys Leu
                325                 330                 335

Val Ile Asn Gln Ser Arg Val Glu Leu Val Lys Lys Pro Glu Asn Leu
            340                 345                 350

Asp Arg Asp Ile Val Thr Thr Pro Thr Phe Ile Ile Asn Asp Ile Leu
        355                 360                 365

Arg Asn Thr Val Leu Pro Lys Cys Tyr Gly Lys Thr Asp Ile Glu Ile
    370                 375                 380

Leu Gln Leu Lys Phe Ala Asp Ile Ala Cys Gly Ser Gly Ala Phe Leu
385                 390                 395                 400

Leu Glu Leu Phe Gln Leu Leu Asn Asp Thr Leu Val Asp Tyr Tyr Leu
                405                 410                 415

Ser Ser Asp Thr Ser Gln Leu Ile Pro Thr Gly Ile Gly Thr Tyr Lys
            420                 425                 430

Leu Ser Tyr Glu Ile Lys Arg Lys Val Leu Leu Ser Cys Ile Phe Gly
        435                 440                 445

Ile Asp Lys Asp Leu Asn Ala Val Glu Ala Ala Lys Phe Gly Leu Leu
    450                 455                 460

Leu Lys Leu Leu Glu Gly Glu Asp Val Gln Ser Ile Ala Asn Ile Arg
465                 470                 475                 480

Pro Val Leu Pro Asp Leu Leu Asp Asn Ile Leu Phe Gly Asn Ser Leu
                485                 490                 495

Leu Glu Pro Glu Lys Val Glu Leu Asp His Gln Val Glu Val Asn Pro
            500                 505                 510

Leu Asp Phe Ser Asp Leu Lys Phe Asp Val Ile Val Gly Asn Pro Pro
        515                 520                 525

Tyr Met Lys Ser Glu Asp Met Lys Asn Ile Thr Pro Leu Glu Leu Pro
    530                 535                 540

```
Leu Tyr Lys Lys Asn Tyr Val Ser Ala Tyr Lys Gln Phe Asp Lys Tyr
545                 550                 555                 560

Phe Leu Phe Leu Glu Arg Gly Leu Ala Leu Leu Lys Glu Glu Gly Ile
            565                 570                 575

Leu Gly Tyr Ile Val Pro Ser Lys Phe Thr Lys Val Gly Ala Gly Lys
        580                 585                 590

Lys Leu Arg Glu Leu Leu Thr Asp Lys Gly Tyr Leu Asp Ser Ile Val
    595                 600                 605

Ser Phe Gly Ala Asn Gln Ile Phe Gln Asp Lys Thr Thr Tyr Thr Cys
610                 615                 620

Leu Leu Ile Leu Arg Lys Thr Pro His Thr Asp Phe Lys Tyr Ala Glu
625                 630                 635                 640

Val Arg Asn Leu Ile Asp Trp Lys Val Arg Lys Ala Asp Ala Met Glu
                645                 650                 655

Phe Ser Ser Gln Gln Leu Ser Thr Leu Gln Ser Asp Ala Trp Ile Leu
            660                 665                 670

Ile Pro Ser Glu Leu Ile Ser Val Tyr His Gln Ile Leu Ala Gln Ser
        675                 680                 685

Gln Lys Leu Glu Asp Ile Val Gly Ile Asp Asn Ile Phe Asn Gly Ile
    690                 695                 700

Gln Thr Ser Ala Asn Asp Val Tyr Ile Phe Val Pro Thr His Glu Asp
705                 710                 715                 720

Thr Glu Asn Tyr Tyr Phe Ile Lys Lys Gly Gln Glu Tyr Lys Ile Glu
                725                 730                 735

Lys Glu Ile Thr Lys Pro Tyr Phe Lys Thr Thr Ser Gly Glu Asp Asn
            740                 745                 750

Leu Tyr Thr Tyr Arg Thr Phe Lys Pro Asn Ala Arg Val Ile Tyr Pro
        755                 760                 765

Tyr Thr Gln Thr Glu Ser Ser Val Glu Leu Ile Pro Leu Asp Glu Ile
    770                 775                 780

Arg Glu Ile Phe Pro Leu Ala Tyr Lys Tyr Leu Met Ser Leu Lys Phe
785                 790                 795                 800

Val Leu Ser Ser Pro Lys Arg Asp Ile Lys Pro Arg Pro Lys Thr Thr
                805                 810                 815

Asn Glu Trp His Arg Tyr Gly Arg His Gln Ser Leu Asp Asn Cys Gly
            820                 825                 830

Leu Ser Gln Lys Ile Ile Gly Val Leu Ser Val Gly Asp Lys Tyr
        835                 840                 845

Ala Ile Asp Thr Tyr Gly Thr Leu Ile Ser Ser Gly Gly Thr Ala Gly
850                 855                 860

Tyr Cys Val Val Ala Leu Pro Asp Asp Cys Lys Tyr Ser Ile Tyr Tyr
865                 870                 875                 880

Leu Gln Ala Ile Leu Asn Ser Lys Tyr Leu Glu Trp Phe Ser Ala Leu
                885                 890                 895

His Gly Glu Val Phe Arg Gly Gly Tyr Ile Ala Arg Gly Thr Lys Val
            900                 905                 910

Leu Lys Asn Leu Pro Ile Arg Lys Ile Asp Phe Asp Asn Leu Glu Glu
        915                 920                 925

Ala Asn Leu His Asp Leu Ile Ala Thr Lys Gln Lys Glu Leu Ile Glu
    930                 935                 940

Ile Tyr Asp Lys Ile Asp Val Asn Val Asn Asn Lys Arg Val Leu Thr
945                 950                 955                 960
```

```
Pro Leu Gln Arg Met Phe Lys Arg Glu Lys Glu Val Leu Asp Gln Leu
                965                 970                 975

Leu Ser Arg Leu Tyr Asn Leu Gly Val Asp Asp Ser Leu Ile Pro Tyr
            980                 985                 990

Ile Lys Asp Leu Tyr Glu Ala His
        995                 1000

<210> SEQ ID NO 5
<211> LENGTH: 24
<212> TYPE: DNA
<213> ORGANISM: unknown
<220> FEATURE:
<223> OTHER INFORMATION: inverse PCR primer

<400> SEQUENCE: 5
tataagctct ttttgcttgg tcgc                                          24

<210> SEQ ID NO 6
<211> LENGTH: 24
<212> TYPE: DNA
<213> ORGANISM: unknown
<220> FEATURE:
<223> OTHER INFORMATION: inverse PCR primer

<400> SEQUENCE: 6
aagagttctg accccattgc aacg                                          24

<210> SEQ ID NO 7
<211> LENGTH: 24
<212> TYPE: DNA
<213> ORGANISM: unknown
<220> FEATURE:
<223> OTHER INFORMATION: inverse PCR primer

<400> SEQUENCE: 7
tacctgttgg aattaattga gaag                                          24

<210> SEQ ID NO 8
<211> LENGTH: 24
<212> TYPE: DNA
<213> ORGANISM: unknown
<220> FEATURE:
<223> OTHER INFORMATION: inverse PCR primer

<400> SEQUENCE: 8
tcggtactta taagctgtct tatg                                          24

<210> SEQ ID NO 9
<211> LENGTH: 24
<212> TYPE: DNA
<213> ORGANISM: unknown
<220> FEATURE:
<223> OTHER INFORMATION: Primer

<400> SEQUENCE: 9
cccagagtaa acggactctc ttcc                                          24

<210> SEQ ID NO 10
<211> LENGTH: 43
<212> TYPE: DNA
<213> ORGANISM: unknown
<220> FEATURE:
<223> OTHER INFORMATION: forward primer
```

-continued

```
<400> SEQUENCE: 10
ccaactgcag gaataaccca tggttcatga tcataagctt gaa                    43

<210> SEQ ID NO 11
<211> LENGTH: 31
<212> TYPE: DNA
<213> ORGANISM: unknown
<220> FEATURE:
<223> OTHER INFORMATION: reverse primer

<400> SEQUENCE: 11
ccttccggat ccttaatata agggatcaag g                                 31

<210> SEQ ID NO 12
<211> LENGTH: 33
<212> TYPE: DNA
<213> ORGANISM: unknown
<220> FEATURE:
<223> OTHER INFORMATION: reverse primer

<400> SEQUENCE: 12
ccttccggat ccacgtaatt tttcggcaga tgc                               33
```